United States Patent
Zhang

(10) Patent No.: US 10,550,751 B2
(45) Date of Patent: Feb. 4, 2020

(54) METHOD AND SYSTEM FOR EXHAUST PARTICULATE MATTER SENSING

(71) Applicant: Ford Global Technologies, LLC, Dearborn, MI (US)

(72) Inventor: Xiaogang Zhang, Novi, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 16/058,114

(22) Filed: Aug. 8, 2018

(65) Prior Publication Data

US 2018/0347437 A1    Dec. 6, 2018

Related U.S. Application Data

(62) Division of application No. 15/145,117, filed on May 3, 2016, now Pat. No. 10,100,703.

(51) Int. Cl.
| | | |
|---|---|---|
| *G01N 15/00* | (2006.01) | |
| *F01N 13/00* | (2010.01) | |
| *G01N 15/06* | (2006.01) | |
| *G01M 15/10* | (2006.01) | |

(52) U.S. Cl.
CPC ......... *F01N 13/008* (2013.01); *G01M 15/102* (2013.01); *G01N 15/0606* (2013.01); *G01N 15/0656* (2013.01); *F01N 2560/05* (2013.01); *G01N 2015/0046* (2013.01)

(58) Field of Classification Search
CPC .. F01N 13/008; F01N 2560/05; F01N 3/0214; G01N 15/0656; G01N 15/0606; G01N 2015/0046; G01M 15/102
See application file for complete search history.

(56) References Cited

U.S. PATENT DOCUMENTS

| | | |
|---|---|---|
| 7,497,138 B2 | 3/2009 | Kubinski et al. |
| 2015/0355067 A1 | 12/2015 | Zhang et al. |
| 2016/0238629 A1 | 8/2016 | Ireland et al. |
| 2016/0370301 A1 | 12/2016 | Oh et al. |
| 2017/0058746 A1 | 3/2017 | Zhang |
| 2017/0080436 A1 | 3/2017 | Chin et al. |
| 2017/0131185 A1 | 5/2017 | Koike et al. |
| 2017/0254251 A1 | 9/2017 | Zhang |

*Primary Examiner* — Blake A Tankersley

(74) *Attorney, Agent, or Firm* — Geoffrey Brumbaugh; McCoy Russell LLP

(57) ABSTRACT

Methods and systems are provided for a particulate matter (PM) sensor assembly positioned downstream of a diesel particulate filter in an exhaust system. In one example, a method may include rotating the PM sensor assembly inside an exhaust passage to generate an output, the rotation based on exhaust flow conditions within the exhaust passage. By rotating the PM sensor assembly via a bearing, a rate of soot particulate accumulation on a sensor element of the assembly may be maintained at a desired level, and independent of a direction of exhaust flow inside the exhaust passage.

11 Claims, 10 Drawing Sheets

METHOD AND SYSTEM FOR EXHAUST PARTICULATE MATTER SENSING

CROSS REFERENCE TO RELATED APPLICATION

The present application is a divisional of U.S. patent application Ser. No. 15/145,117, entitled "METHOD AND SYSTEM FOR EXHAUST PARTICULATE MATTER SENSING," filed on May 3, 2016. The entire contents of the above-referenced application are hereby incorporated by reference in its entirety for all purposes.

FIELD

The present application relates to sensing particulate matter in an exhaust system.

BACKGROUND/SUMMARY

Engine emission control systems may utilize various exhaust sensors. One example sensor may be a particulate matter sensor, which indicates particulate matter mass and/or concentration in the exhaust gas. In one example, the particulate matter sensor may operate by accumulating particulate matter over time and providing an indication of the degree of accumulation as a measure of exhaust particulate matter levels. The particulate matter sensor may be located upstream and/car downstream of a diesel particulate filter, and may be used to sense particulate matter loading on the particulate filter and diagnose operation of the particulate filter.

An example PM sensor is shown by Zhang et. al. in US 2015/0355067 A1. Therein, the PM sensor includes a cylindrical protection tube having perforations, and a sensor element is positioned inside the tube facing towards the perforations. The PM sensor is fixed to an exhaust passage downstream of a particulate filter in such a way that the perforations are located on a downstream surface of the protection tube, facing towards a tail end of the exhaust passage. In such a configuration, exhaust gas flowing through the exhaust passage may experience pressure variations along the exterior of the protection tube. For example, a higher static pressure may be created at the downstream surface of the protection tube than along the sides of the protection tube. Because of the higher static pressure at the downstream surface relative to the side surfaces, exhaust gas may be drawn in towards the downstream surface of the PM sensor. In particular, the exhaust gases may be drawn towards the perforations on the downstream surface of the protection tube, and the exhaust may enter the PM sensor via the perforations in a direction opposite to the direction of exhaust flow inside the exhaust passage.

The inventors herein have recognized potential issues with such systems. As an example, the above-mentioned configuration works under the assumption that the exhaust flow direction inside the exhaust passage is constant. Since the sensor is fixed to the exhaust passage, only when the perforations of the protection tube are positioned along a surface that is diametrically opposite to the surface facing the onslaught of exhaust flow will the perforations be coincident with higher static pressure side of the tube. However, if the direction of flow of exhaust inside the exhaust passage changes (e.g., due to changes in engine speed, load, cylinder deactivation, exhaust valve timing, and the like), the perforations may no longer be located on the side with the higher static pressure. In some configurations, the exhaust passage may comprise multiple passages or pathways, some of which are diverging and others that are converging. Together, these pathways may direct exhaust gas through various components of the engine system. If the PM sensor is positioned at an intersection of two orthogonal passages, for example, the direction of exhaust flow may change by 90° when exhaust flow is changed from one passage to the other. In such cases, the perforations on the tube may be in the higher static pressure side when exhaust flows though one of the passages but not when exhaust flows through the second orthogonal passage, for example. If the exhaust flow direction changes by 90° when exhaust flows through the second passage, the perforations on the tube may no longer be located on the higher static pressure side relative to the second passage. Instead, the perforations may now be located on a lower pressure side. Thus, exhaust gas may be pushed away from the perforations thereby reducing the flow of exhaust into the sensor. As a result, the sensitivity of the sensor may be reduced. With reduced sensitivity, the soot sensor may not be able to determine the leakage of the particulate filter in a reliable way. Thus, errors in the sensor may lead to a false indication of DPF degradation and unwarranted replacement of functioning filters.

In one example, the issues described above may be partially addressed by a method comprising, while exhaust is flowing through an exhaust passage, generating an output from a rotatable particulate matter (PM) sensor assembly coupled to the exhaust passage, rotation of the rotatable PM sensor assembly changing as exhaust flow conditions change. In this way, by rotating the PM sensor assembly based on the exhaust flow conditions, an entrance to the PM sensor may be automatically adjusted to be on a side with higher static pressure, thereby increasing the amount of exhaust flow into the PM sensor assembly.

As one example, an exhaust PM sensor assembly may be positioned downstream of an exhaust particulate filter in an exhaust passage. The PM sensor assembly may include a cylindrical housing rotatably mounted to the exhaust passage via a bearing and a sensor element may be positioned within the housing. The housing may additionally include an opening formed only one side, and as such, the opening may be positioned between a pair of perforated flow plates attached to the housing on either side of the opening. The arrangement of the bearing may provide for a free rotation of the PM sensor assembly around a central axis on the housing with reduced friction between the housing and a top surface of the exhaust passage. For example, when a direction of exhaust flow inside the exhaust passage changes by a threshold amount, the PM sensor assembly may rotate inside the exhaust passage in such a way that the opening of the assembly is positioned on a downstream side where the static pressure is higher. In this way, an increased amount of particulates in the exhaust may be directed into the opening towards the sensor element. As such, the rotation of the PM sensor assembly may be one of a passive rotation or an active rotation. During passive rotation, the flow plates attached to the assembly may sense the direction of exhaust flow inside the exhaust passage, and accordingly rotate the assembly via the bearing, for example. During active rotation, the PM sensor assembly may be rotated via a motor coupled to the assembly. Herein, the output of the motor may be adjusted based on the sensed exhaust flow conditions.

The technical effect of rotating the PM sensor assembly inside the exhaust passage based on sensed exhaust flow conditions is that the opening on the housing is automatically moved to a downstream side where the static pressure is higher. Thus, exhaust flowing through the exhaust passage will be diverted around the assembly, and forced to enter the assembly through the opening between the perforated flow plates. In this way, the amount of exhaust entering the assembly may be increased. Exhaust entering though the opening is then directed towards the sensor element that is placed facing towards the opening. Particulates in the exhaust are accumulated across the sensor element. Thus, the amount of exhaust gas and thereby the amount of particulates being deposited on the sensor element may become independent of the incoming exhaust flow direction, thereby measuring PM exiting the particulate filter more accurately and reliably. Further, larger particulates and/or water droplets may be trapped by the flow plates. Therefore, the sensor element may be protected from impingement of water droplets and larger particulates. Overall, these characteristics of the sensor may cause an output of the sensor to be more accurate, thereby increasing the accuracy of estimating particulate loading on a particulate filter.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
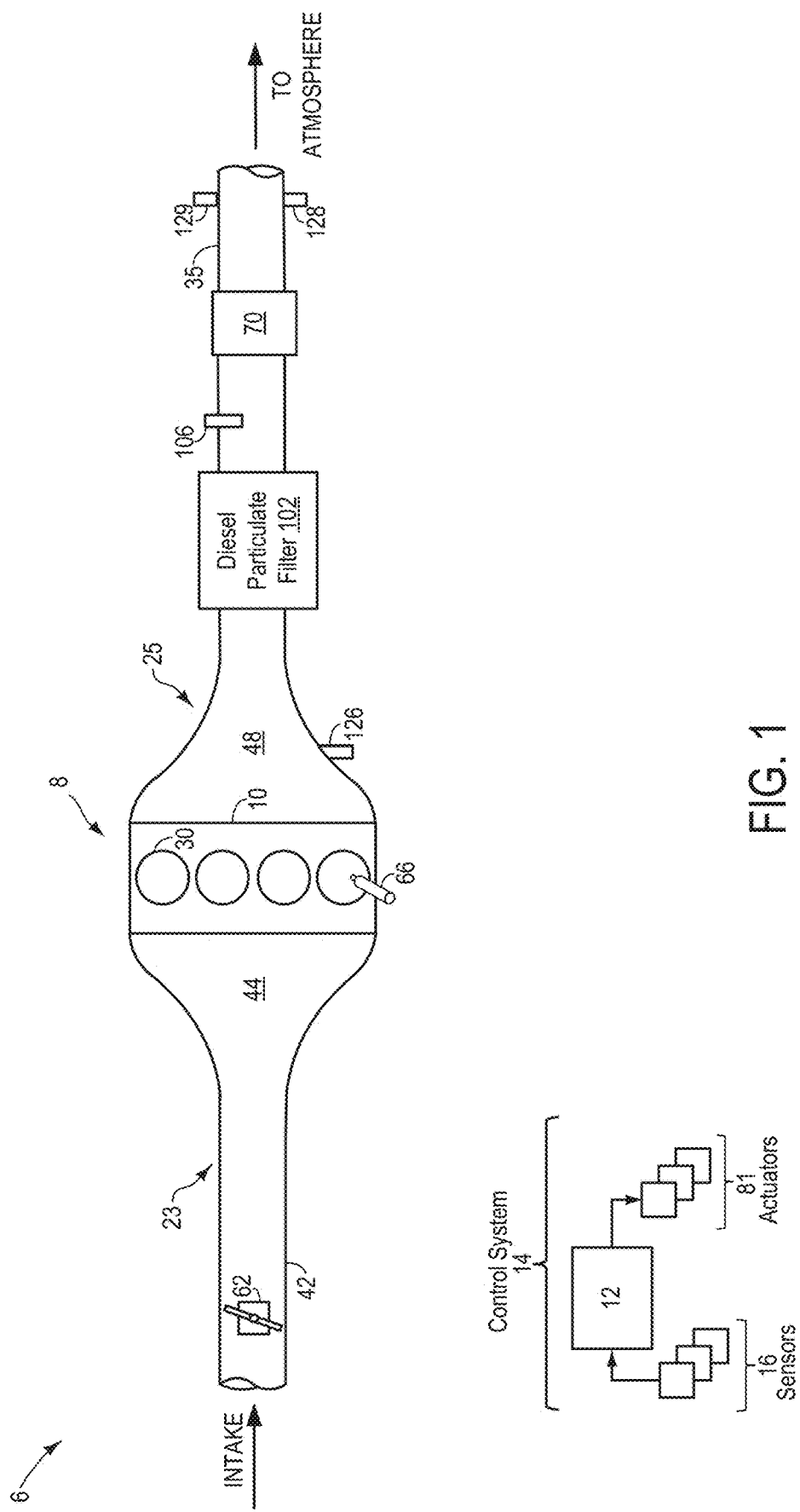
FIG. 1 shows a schematic diagram of an engine and a rotatable particulate matter (PM) sensor assembly positioned in an exhaust flow.
Figure 2:
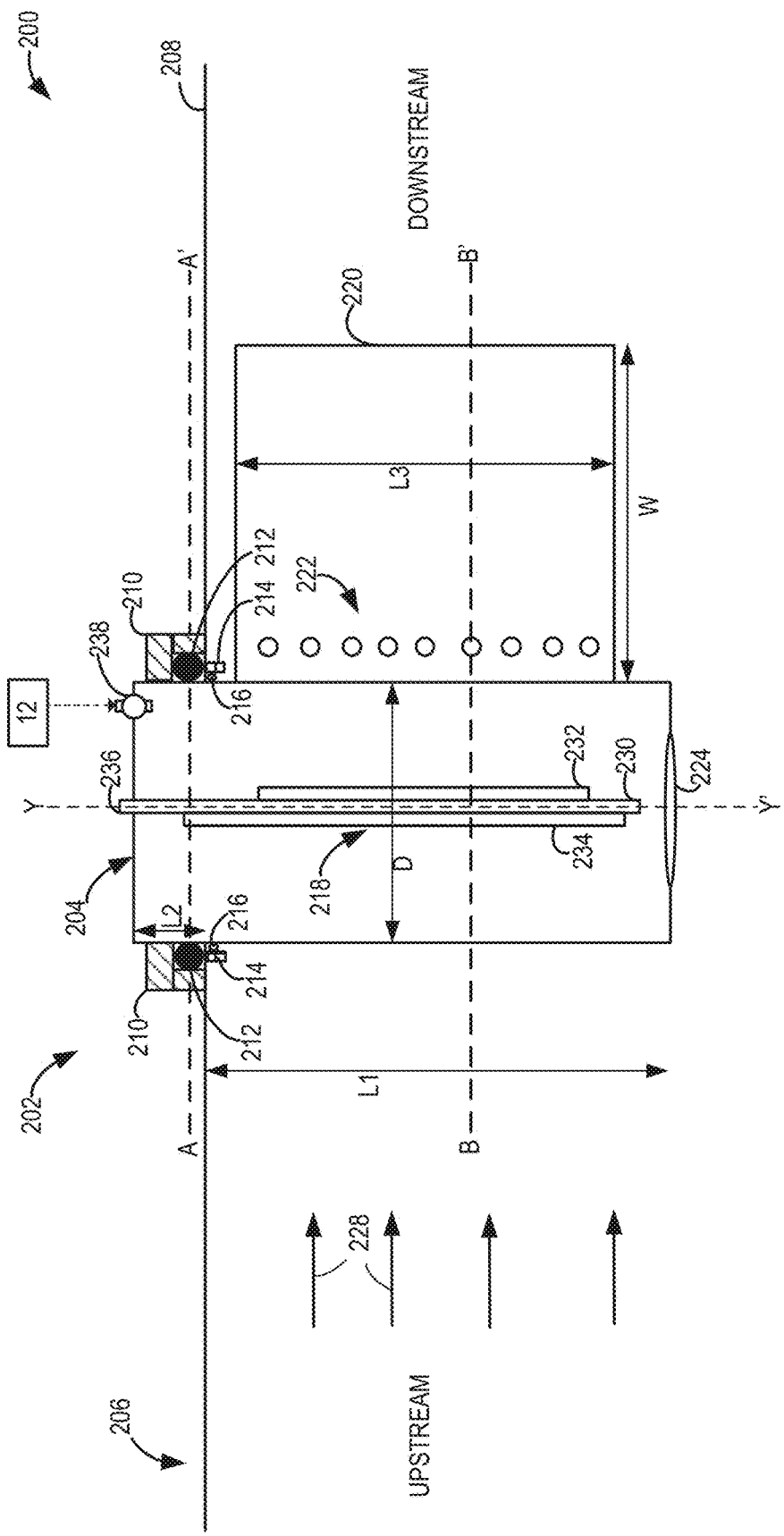
FIG. 2 shows a schematic diagram of the PM sensor including a cylindrical housing mounted to an exhaust passage via a bearing, the housing including a pair of flow plates mounted to one side of the housing.
Figure 3A:
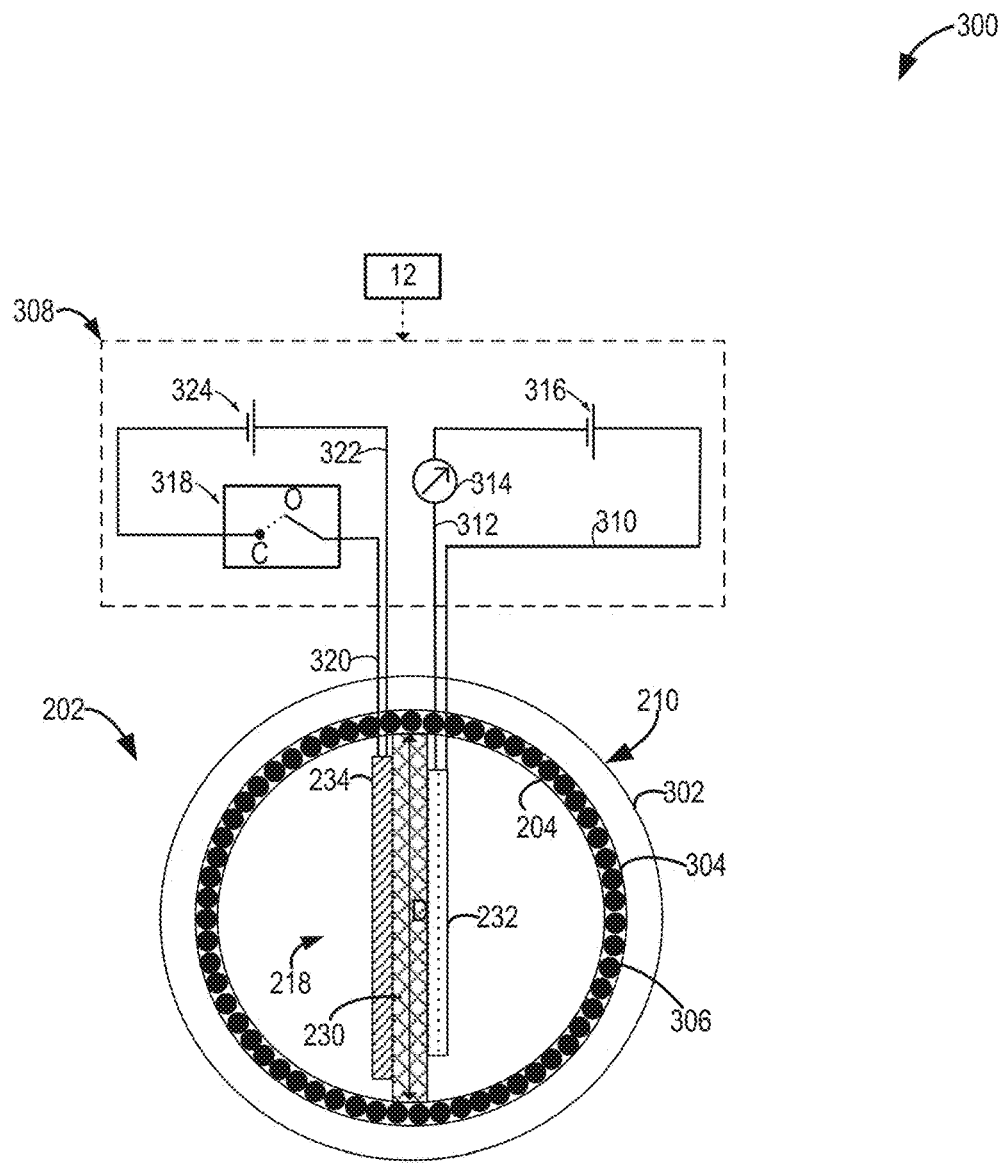
FIGS. 3A-3B show cross-sectional views of the housing, the bearing, the flow plates, an opening formed between the flow plates, and a sensor element positioned within the housing facing towards the opening.
Figure 3A:
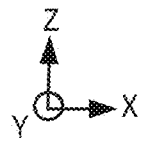
Figure 3B:
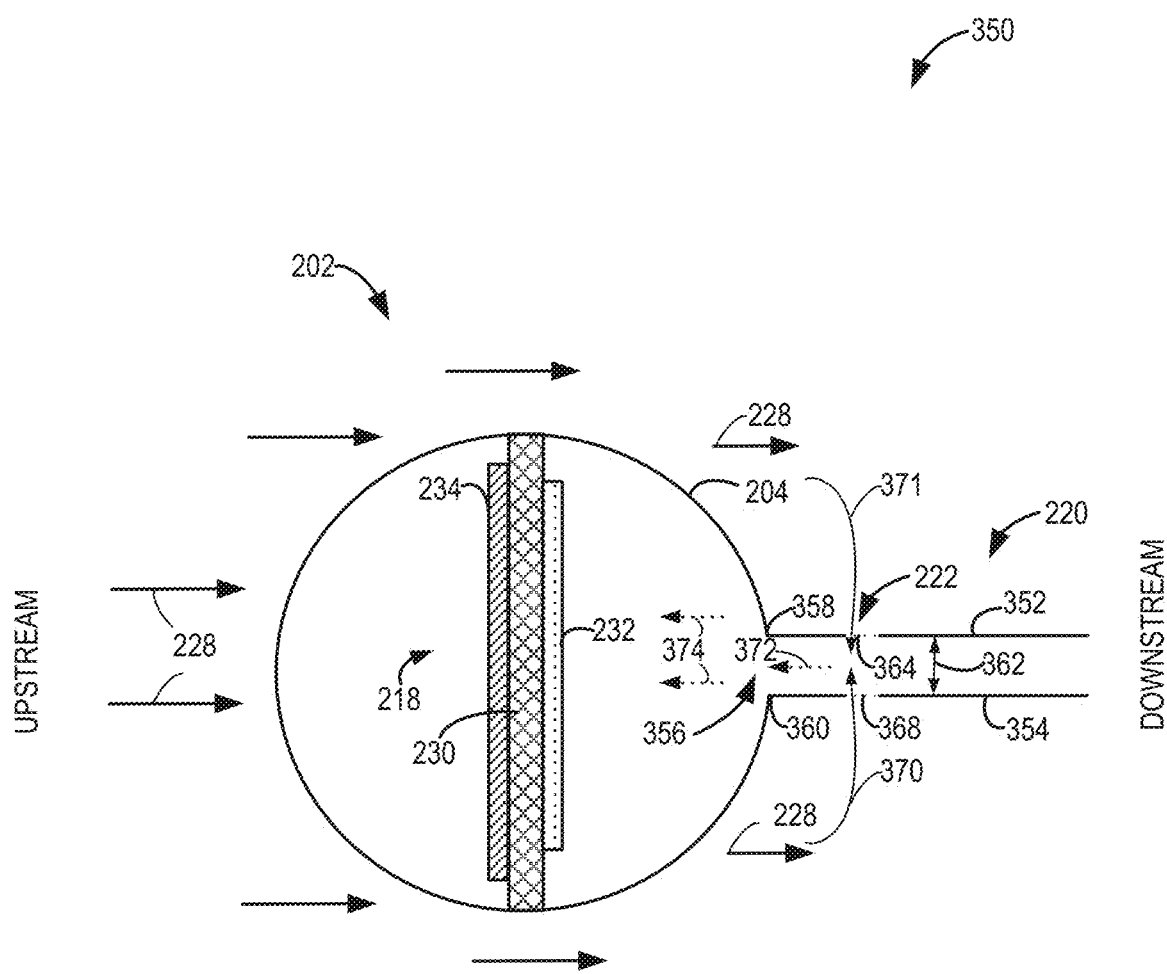
Figure 4:
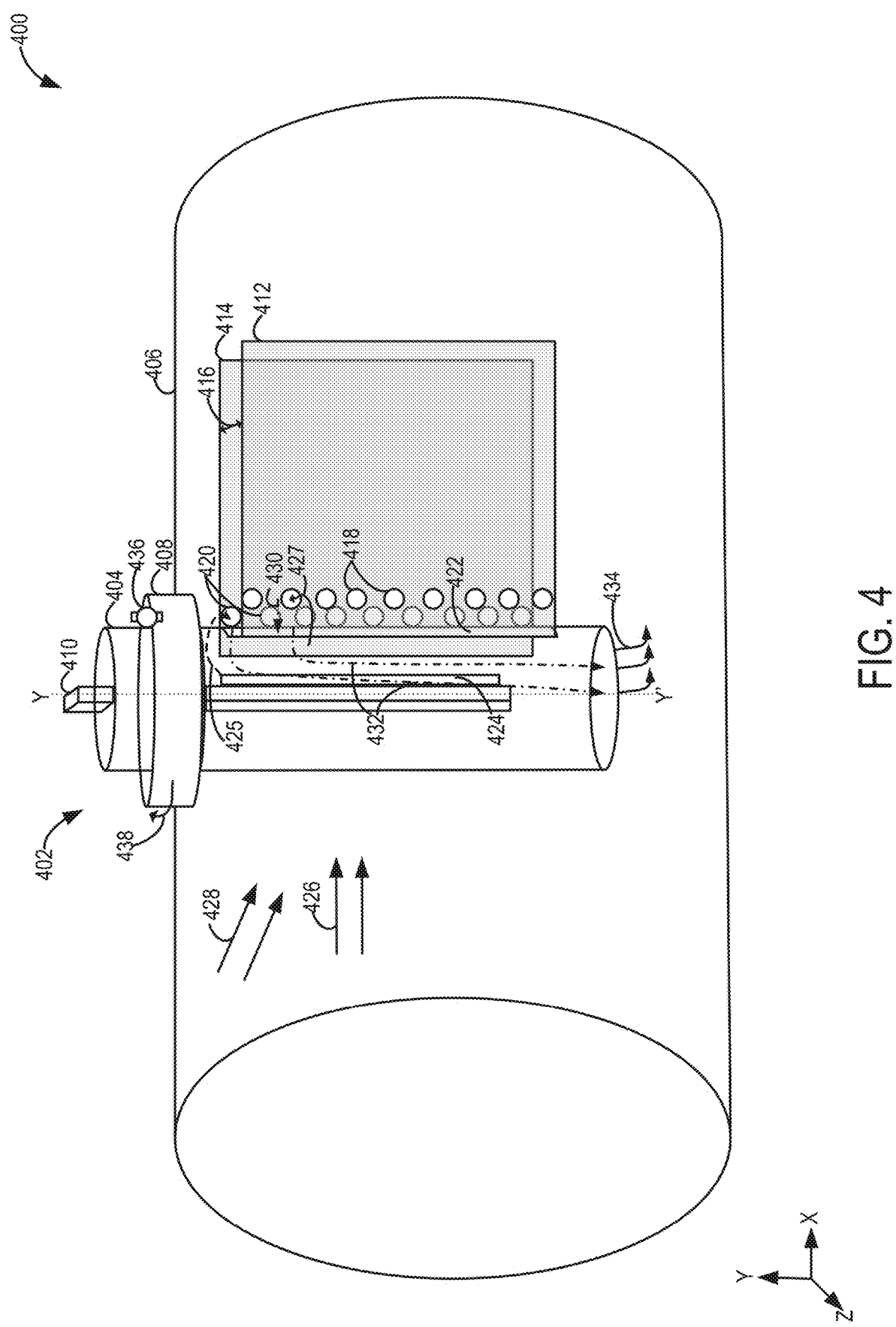
FIG. 4 shows a schematic diagram of the PM sensor assembly showing exhaust flowing into the PM sensor assembly via a plurality of perforations formed on the flow plates.
Figure 8:
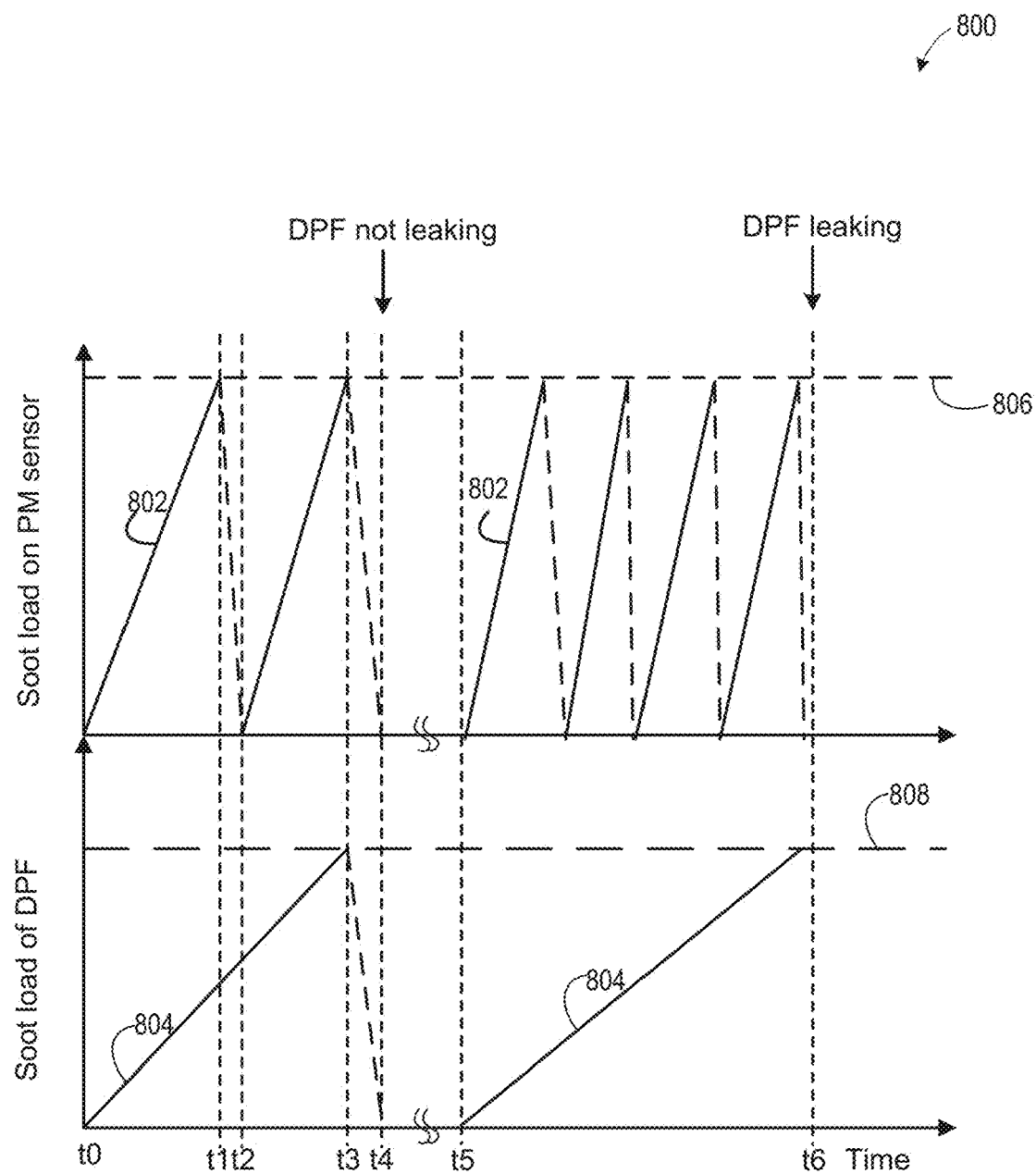
FIG. 8 shows an example relationship between a soot load on the PM sensor assembly, and a soot load on a particulate filter positioned upstream of the PM sensor assembly.
Figure 9:
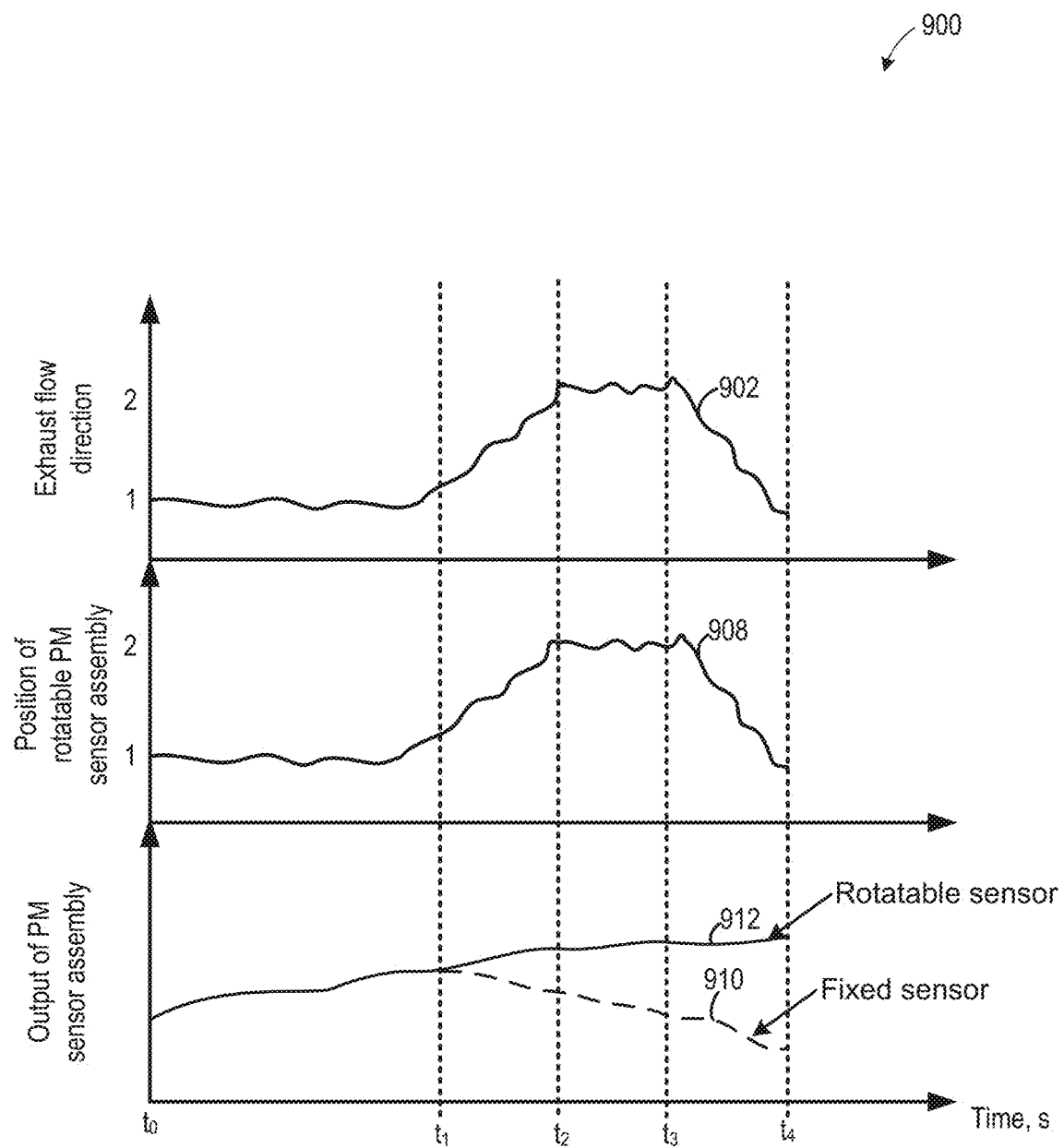
FIG. 9 shows an example relationship between an exhaust flow direction, a position of a rotatable PM sensor assembly, and an output of the PM sensor assembly.

The following description relates to systems and methods for sensing particulate matter (PM) in an exhaust flow of an engine system, such as the engine system shown in FIG. 1. A rotatable PM sensor assembly may be coupled to an exhaust passage of the engine system as shown in FIG. 2. As such, the PM sensor assembly may include a cylindrical housing mounted to the exhaust passage via a bearing. In addition, the PM sensor assembly may include an opening formed on one side of the housing. Two parallel flow plated may be mounted on either side of the opening. Cross-sectional views of the housing with the bearing, the flow plates, and the opening are shown in FIGS. 3A-3B. The flow plate may additionally include a plurality of perforations configured to receive exhaust from the exhaust passage and direct the exhaust through the opening towards a sensor element positioned within the housing as shown in FIG. 4. In an example embodiment, the PM sensor assembly may rotate passively via the bearing based on sensed exhaust flow conditions. In another example, the assembly may include a motor, and in addition, a controller may be configured to perform a control routine, such as an example routine of FIG. 5 to rotate the PM sensor assembly based on the sensed exhaust flow conditions. Herein, rotating the PM sensor assembly may include rotating the assembly to allow exhaust to enter the housing though the opening towards the sensor element in a direction opposite to the direction of flow of exhaust in the exhaust passage. Soot particles in the exhaust are then collected across electrodes formed on the sensor element. An example relationship between an exhaust flow direction, a position of the rotatable PM sensor assembly, and an output of the assembly is shown in FIG. 9. The controller may intermittently clean the PM sensor assembly (FIG. 6) to enable continued PM monitoring. Furthermore, the controller may be configured to perform a routine, such as an example routine of FIG. 7 to regenerate the exhaust particulate filter based on a time between PM sensor regenerations. An example of filter diagnostics is shown in FIG. 8. In this way, the functioning of the PM sensor to estimate the filtering capabilities of the DPF (and thereby to detect DPF leaks) may be increased.

FIG. 1 shows a schematic depiction of a vehicle system 6. The vehicle system 6 includes an engine system 8. The engine system 8 may include an engine 10 having a plurality of cylinders 30. Engine 10 includes an engine intake 23 and an engine exhaust 25. Engine intake 23 includes a throttle 62 fluidly coupled to the engine intake manifold 44 via an intake passage 42. The engine exhaust 25 includes an exhaust manifold 48 eventually leading to an exhaust passage 35 that routes exhaust gas to the atmosphere. Throttle 62 may be located in intake passage 42 downstream of a boosting device, such as a turbocharger (not shown), and upstream of an after-cooler (not shown). When included, the after-cooler may be configured to reduce the temperature of intake air compressed by the boosting device.

Engine exhaust 25 may include one or more emission control devices 70, which may be mounted in a close-coupled position in the exhaust. One or more emission control devices may include a three-way catalyst, lean NOx filter, SCR catalyst, etc. Engine exhaust 25 may also include diesel particulate filter (DPF) 102, which temporarily filters PMs from entering gases, positioned upstream of emission control device 70. In one example, as depicted, DPF 102 is a diesel particulate matter retaining system. DPF 102 may have a monolith structure made of, for example, cordierite or silicon carbide, with a plurality of channels inside for filtering particulate matter from diesel exhaust gas. Tailpipe exhaust gas that has been filtered of PM, following passage through DPF 102, may be measured in a PM sensor 106 and further processed in emission control device 70 and expelled to the atmosphere via exhaust passage 35. In the depicted example, PM sensor 106 is a resistive sensor that estimates the filtering efficiency of the DPF 102 based on a change in conductivity measured across the electrodes of the PM sensor. A schematic view 200 of the PM sensor 106 is shown at FIG. 2, as described in further detail below.

The vehicle system 6 may further include control system 14. Control system 14 is shown receiving information from a plurality of sensors 16 (various examples of which are described herein) and sending control signals to a plurality of actuators 81 (various examples of which are described herein). As one example, sensors 16 may include exhaust flow rate sensor 126 configured to measure a flow rate of exhaust gas through the exhaust passage 35, exhaust gas sensor (located in exhaust manifold 48), temperature sensor 128, pressure sensor 129 (located downstream of emission control device 70), and PM sensor 106. Other sensors such as additional pressure, temperature, air/fuel ratio, exhaust flow rate and composition sensors may be coupled to various locations in the vehicle system 6. As another example, the actuators may include fuel injectors 66, throttle 62, DPF valves that control filter regeneration (not shown), a motor actuator controlling PM sensor assembly rotation, switch of electric circuit, etc. The control system 14 may include a controller 12. The controller 12 may be configured with computer readable instructions stored on non-transitory memory. The controller 12 receives signals from the various sensors of FIG. 1, processes the signals, and employs the various actuators of FIG. 1 to adjust engine operation based on the received signals and instructions stored on a memory of the controller. As an example, while operating the PM sensor to accumulate soot particulates, the controller send a control signal to an electric circuit to apply a voltage to electrodes of a sensor element of the PM sensor assembly to trap the charged particulates onto the surface of sensor electrodes of a sensor element. As another example, during PM sensor assembly regeneration, the controller may send a control signal to a regeneration circuit to close a switch in the regeneration circuit for a threshold time to apply a voltage to a heating element coupled to electrodes to heat the electrodes of the sensor element. In this way, the electrodes are heated to burn off soot particles deposited on the surface of the electrodes. In yet another example, the controller may rotate the PM sensor assembly coupled to the exhaust passage to increase particulate matter accumulation on the sensor element. Rotating the PM sensor assembly includes adjusting an actuator of a motor coupled to the assembly to rotate the assembly by a threshold amount based on sensed exhaust flow conditions. Herein, the controller may adjust the output of the motor to control the amount of rotation of the assembly. In this way, the PM sensor assembly may be rotated so that a larger amount of exhaust enters the assembly along a higher static pressure side of the assembly. Example routines are described herein with reference to FIGS. 5-7.

Turning now to FIG. 2, a schematic view 200 of an example embodiment of a particulate matter (PM) sensor assembly 202 (such as PM sensor 106 of FIG. 1) is shown. The PM sensor assembly 202 may be configured to measure PM mass and/or concentration in the exhaust gas, and as such, may be coupled to an exhaust passage or pipe 206 (e.g., such as the exhaust passage 35 shown in FIG. 1), upstream or downstream of a diesel particulate filter (such as DPF 102 shown in FIG. 1).

In the schematic view 200, the PM sensor assembly 202 is disposed inside the exhaust passage 206 with exhaust gases flowing (along X-axis) from downstream of the diesel particulate filter towards an exhaust tailpipe, as indicated by arrows 228. With reference to the PM sensor assembly 202, exhaust flows from an upstream side towards a downstream side of the assembly as indicate in FIG. 2 in the direction indicated by arrow 228. Herein, the downstream side is closer to an exhaust tailpipe.

The PM sensor assembly 202 (hereafter interchangeably referred to as assembly or PM sensor) includes a hollow, cylindrical tube (hereafter interchangeable referred to as housing) 204 of diameter D, positioned inside the exhaust passage 206. A larger portion of the housing 204 extends to a length L1 inside the exhaust passage 206 while a smaller portion of the housing 204 (of length, L2) remains outside the exhaust passage 206. Together, the length of the housing is L wherein L=L1+L2. Herein, a central axis Y-Y' of the housing 204 is orthogonal to the direction of exhaust flow inside the exhaust passage 206 (indicated by arrow 228). The housing 204 is an outer protection tube that protects a sensor element 218 that is suspended there within. The housing 204 is rotatably coupled to a top 208 of the exhaust passage 206 via a bearing 212 which is arranged between a sensor boss or cap 210 and the housing 204. To elucidate further, the smaller portion of the housing 204 is coupled to the sensor cap 210, and the bearing 212 is arranged between the smaller portion of the housing 204 and the sensor boss 210. Specifically, the bearing 212 is arranged in between three surfaces, an inner surface of the sensor boss 210, an outer surface of the housing 204, and an outer surface of a gasket holder 214. Herein, the gasket holder 214 holds a gasket 216 that seals the PM sensor assembly 202 such that there is no exhaust gas leak from the top of the assembly 202.

The bearing 212 enables rotational movement of the PM sensor assembly 202 about the central axis Y-Y' relative to the exhaust passage 206. Thus, the exhaust passage 206 is fixed, and the PM sensor assembly 202 rotates inside the exhaust passage 206 via the bearing 212. Specifically, the housing 204, the sensor cap 210, the gasket holder 214, the gasket 216, and the sensor element 218 are all coupled together, and rotate together as a single entity inside the assembly via the bearing 212. As such, the bearing 212 is a device that allows two parts to move with respect to another with reduced friction. Specifically, the bearing 212 reduces friction between the housing 204 and the top 208 of the exhaust passage 206. By mounting the PM sensor assembly 202 on the exhaust passage 206, the speed and efficiency of rotation of the assembly in the exhaust passage 206 may be enhanced. Various kinds of bearings may be used without deviating from the scope of the disclosure. Some examples of bearings may include ball bearings, roller bearings, needle roller bearings, tapered roller bearing, spherical roller bearings, thrust bearings, and the like. An example of ball bearings is shown in FIG. 3A.

Turning to FIG. 3A, a cross-sectional view 300 of the PM sensor assembly 202 in a plane along line A-A' of FIG. 2 is shown. Herein, a cross-section of the sensor cap 210 and the housing 204 is shown. The sensor cap 210 includes an outer surface 302 and an inner surface 304. The distance between the outer surface 302 and the inner surface 304 constitutes the thickness of the sensor cap 210. The sensor boss 210 is typically manufactured from high-density stainless steel. A plurality of ball bearings 306 are concentrically placed between the inner surface 304 of the sensor cap 210 and the housing 204. Specifically, the plurality of ball bearings are arranged in an annular gap formed between the housing 204 and the sensor cap 210. Each ball bearing is predominantly spherical in shape and is in face sharing contact with ball bearing on either side, and further in face sharing contact with both the inner surface 304 of the sensor cap 210 and an outer surface of the housing 204. The radius, r, of each ball bearing and the total number, n of ball bearings used may be based on the radii of each of the sensor cap 210 and the housing 204, for example. In addition, as described previously with reference to FIG. 2A, the sensor element 218 is mounted within the housing 204 such that the sensor element is coaxial with the central axis Y-Y' of the housing 204. Thus, the arrangement of the plurality of ball bearings 306 in the annular gap between the housing 204 allows for the housing 204, the sensor element 218, and the sensor cap 210 to rotate together about the central axis Y-Y' (which is perpendicular to the plane of the paper, for example), relative to the exhaust passage 206.

The sensor element 218 includes a substrate 230 attached to diametrically opposite sides of the housing 204. In one example, a width, w of the substrate 230 may be equal to a diameter, D of the housing 204 (e.g., w=D=2R1). Thus, opposite ends of the substrate 230 are in face sharing contact with inner surfaces of the housing 204. Herein, the plurality of bearings 306 and the substrate 230 are in face sharing contact with the outer and the inner surface of the housing 204 respectively. This implies that the substrate 230 of the sensor element 218 is not in direct contact with the plurality of ball bearings 306. In another example, the width w of the substrate 230 may be smaller than the diameter D of the housing (w<D) whereby the substrate 230 may not be in contact with the inner surface of the housing 204.

The substrate 230 of the sensor element 218 may be typically manufactured from highly electrically insulating materials. Possible electrically insulating materials may include oxides such as alumina, zirconia, yttria, lanthanum oxide, silica, and combinations comprising at least one of the foregoing, or any like material capable of inhibiting electrical communication.

Electrodes 232 are formed along a first surface of the substrate 230, and a heating element 234 is formed along a second, opposite surface of the substrate 230. As such, soot particles in the exhaust are collected across the electrodes 232 formed on the substrate 230 of the sensor element 218. The electrodes 232 include a pair of interdigitated electrodes. In one example, the pair of interdigitated electrodes may contain individual planar electrodes forming a "comb" structure. These electrodes may be typically manufactured from metals such as platinum, gold, osmium, rhodium, iridium, ruthenium, aluminum, titanium, zirconium, and the like, as well as, oxides, cements, alloys and combination comprising at least one of the foregoing metals. Each electrode of the interdigitated pair may be composed of the same or different material as the other electrode of the pair. As such, a spacing between the comb "tines" of the two electrodes may typically be in the range from 10 micrometers to 100 micrometers with the linewidth of each individual "tine" being about the same value, although the latter is not necessary. A positive electrode of the interdigitated pair of electrodes 232 is connected to a positive terminal of a voltage source 316 of an electric circuit 308 via a connecting wire 310. Likewise, a negative electrode of the interdigitated pair of electrodes 232 is connected to a measurement device 314 via a connecting wire 312, and further connected to a negative terminal of the voltage source 316 of the electric circuit 308. The interconnecting wires 310 and 312, the voltage source 316 and the measurement device 314 are part of the electric circuit 308 and are housed outside the exhaust passage 206 (as one example, <1 meter away). Further, the voltage source 316 and the measurement device 314 of the electric circuit 308 may be controlled by a controller, such as controller 12 of FIG. 1, so that particulate matter collected at the PM sensor assembly 202 may be used for diagnosing leaks in the DPF, for example. As such, the measurement device 314 may be any device capable of reading a resistance (or current) change across the electrodes, such as a voltmeter (or an ammeter). As PM or soot particles get deposited between the interdigitated pair of electrodes 232, the current measured between the electrodes 232 may start to increase, which is measured by the measurement device 314. The controller 12 may be able to determine the current and infer a corresponding PM or soot load on the interdigitated electrodes 232 of the sensor element 218 of the PM sensor assembly 202. By monitoring the load on the sensor element 218, the exhaust soot load downstream of the DPF may be determined, and thereby used to diagnose and monitor the health and functioning of the DPF.

Various geometries of the sensor electrodes and/or substrate may be used to accumulate particulates across the electrodes of the sensor element. For example, a circular substrate with interdigitated concentric/spiraling electrodes may be used in one example embodiment. As such, the electrodes described thus far are formed on the same substrate, but separated by a gap across the surface of the substrate. In some example embodiments, the electrodes may be formed on different substrates, and may be suspended inside the housing such that the electrodes face one another. Exhaust may be directed in the gap and soot particles may be accumulated in the gap between the electrodes.

The sensor element 218 additionally includes the heating element 234 integrated into the sensor substrate 230. The heating element 234 may comprise, but is not limited to, a temperature sensor, and a heater. Possible materials for the heater and the temperature sensor forming the heating element may include platinum, gold, palladium, and the like; and alloys, oxides, and combinations comprising at least one of the foregoing materials, with platinum/alumina, platinum/palladium, platinum, and palladium. The heating element may be used for regenerating the sensor element 218. Specifically, during conditions when the particulate matter load or soot load of the sensor element 218 is higher than a threshold, the heating element may be operated to burn accumulated soot particles from the surface of sensor. During PM sensor regeneration, the controller 12 may provide a voltage to a voltage source 324, which is needed for operating the heating element 234 and is connected to the heating element 234 via connecting wires 320 and 322. In addition, the controller may close a switch 318 for a threshold time to apply the voltage via the voltage source 324 to the heating element 234 in order to raise the temperature of the heating element 234. Subsequently, when the sensor electrodes are sufficiently clean, the controller may open the switch 318 to stop heating the heating element 234. By intermittently regenerating the sensor element 218, it may be returned to a condition (e.g., unloaded or only partially loaded condition) more suitable for collecting exhaust soot. In addition, accurate information pertaining to the exhaust soot level may be inferred from the sensor regeneration and this information may be used by the controller for diagnosing leaks in the particulate filter.

Returning now to FIG. 2, the schematic view 200 shows the sensor element 218 suspended from a top of the housing 204. In one example, the sensor element 218 may be inserted into the top of the housing 204 such that a larger portion of the sensor element 218 extends to a length, L1 inside the housing 204. A portion of the substrate may remain outside the exhaust passage. As such, the sensor element 218 extends along the Y-axis parallel to the central axis Y-Y' of the housing 204 and perpendicular to a central axis (which is along X-axis) of the exhaust passage 206.

The housing 204 causes a static pressure variation along its exterior and thus, exhaust gases flowing inside the exhaust passage 206 may experience the static pressure variation when they are at or near the PM sensor assembly 202. Specifically, when exhaust is flowing from an upstream side towards a downstream side of the PM sensor assembly 202, a higher static pressure is created at the downstream side compared to exterior side surfaces (e.g., side surfaces located out of the plane of the paper, and inside the plane of the paper) of the PM sensor assembly 202. The higher static pressure at the downstream location may enable an easier drawing in of exhaust gases into PM sensor assembly. In the embodiments described herein, a flow entrance or opening may be advantageously positioned on the downstream location to draw more exhaust into the assembly via the flow entrance (described in detail with reference to FIG. 3B).

In addition, the entire PM sensor assembly 202 is capable of rotating inside the exhaust passage. As such, the rotation of the PM sensor assembly 202 may be one of a passive rotation or an active rotation. Passive rotation of the PM sensor assembly 202 occurs when the PM sensor senses exhaust flow conditions (such as exhaust flow rate, exhaust flow direction, and the like), and automatically rotates based on the sensed exhaust flow conditions, and positions itself in such a way that the flow entrance is positioned on the downstream side as described above. In order for the PM sensor assembly 202 to passively rotate inside the exhaust passage, additional flow plates may be mounted on the PM sensor assembly 202 as described below.

The housing 204 may additionally include a pair of parallel flow plates 220 attached to one side of the housing 204. Specifically, the pair of flow plates 220 is attached to the portion of the housing 204 that extends inside the exhaust passage 206. The flow entrance or opening (not visible in view 200, however visible in cross-sectional view 350 of FIG. 3B) may be formed on the housing 204 in between the pair of flow plates 220. Exhaust flowing inside the exhaust passage 206 may deflect the flow plates 220 and position the flow plates 220 on the downstream side of the exhaust passage 206. Since the flow plates 220 are coupled to the housing 204 and in addition, the housing is rotatably mounted on the exhaust passage 206 via bearing 212, when the flow plates 220 are deflected to the downstream side, the entire PM sensor assembly 202 is automatically rotated via the bearing 212. Herein, the functioning of the flow plates 220 in the exhaust stream may be analogous to the functioning of plate anemometers. While wind deflects the plate anemometers placed on top of buildings, herein, the exhaust flow inside the passage deflects the flow plates and thereby automatically rotates the assembly 202 inside the exhaust passage 206.

Deflecting the flow plates 220 may rotate the PM sensor assembly 202 via the bearing 212 about the central axis Y-Y'. The amount by which the PM sensor assembly 202 is rotated depends on the sensed exhaust flow conditions such as the exhaust flow rate, exhaust flow direction, and the like. For example, when the exhaust flow direction changes, the flow plates 220 may be deflected by a certain amount that is proportional to the amount by which the flow direction changes. If the change is flow direction is larger, and then the deflection of the flow plates will be larger, thereby the assembly will be rotated by a larger amount. Likewise, when the change in flow direction is smaller, then the deflection of the flow plates will be smaller, thereby the assembly will be rotated by a smaller amount.

Deflecting or rotating the PM sensor assembly 202 includes rotating the assembly such that the flow entrance is positioned on the downstream side (as shown below in FIG. 3B). As explained previously, the downstream side has a higher static pressure, and thus exhaust gases may be able to enter the assembly via the flow entrance, which is automatically placed in the downstream side when the incoming exhaust deflects the flow plates 220. The flow plates 220 may additionally include a plurality of perforations or holes 222 formed along the length of the flow plates 220. The plurality of perforations 222 formed on the flow plates 220 are configured to receive exhaust inside the exhaust passage 206 as described in detail in FIG. 3B.

Turning now to FIG. 3B, a cross-sectional view 350 of the PM sensor assembly 202 in a plane along line B-B' of FIG. 2 is shown. Herein, a cross-section of the housing 204 including the sensor element 218, and the pair of flow plates 220 having the perforations is shown.

The housing 204 has a circular cross-section and includes a flow entrance 356 (hereafter interchangeably referred to as opening or cut-out) formed only on one side of the housing 204. A pair of flow plates 220 is mounted to the housing 204 on the same side that includes the flow entrance 356. Specifically, the pair of flow plates 220 includes a first flow plate 352 attached to a first end 358 of the flow entrance 356, and further includes a second flow plate 354 attached to a second opposite end 360 of the flow entrance 356. The first flow plate 352 is separated from the second flow plate 354 by a gap 362. The gap 362 between the pair of parallel flow plates 220 is equal to the width of the flow entrance 356. Herein, the distance between the first end 358 and the second end 360 of the flow entrance 356 constitutes the width of the flow entrance 356. Thus, the flow entrance 356 formed on one side of the housing 204 is contiguous to the gap 362 formed between the pair of flow plates 220.

As explained earlier, the pair of flow plates 220 includes a plurality of perforations 222. In cross-section view 350, a first perforation 364 of the plurality of perforations 222 formed on the first flow plate 352 and a second perforation 368 of the plurality of perforations 222 formed on the second flow plate 354 are shown. The perforations 364 and 368 are indicated as dotted lines. In one example, the plurality of perforations 222 formed on the flow plates 220 are located closer to the flow entrance 356. To elucidate further, the first perforation 364 of the first flow plate 352 is formed proximate to the flow entrance 356, and likewise, the second perforation 368 of the second flow plate 354 is formed proximate to the flow entrance 356. In one example, the first perforation 364 and the second perforation 368 may be similar in size and shape and may be further aligned with respect to each other. In another example, the first and the second perforation may not be similar in size and shape (e.g., a radius of the first perforation may be larger or smaller than a radius of the second perforation) and may further be staggered along the flow plates.

The purpose of the plurality of perforations 222 formed on the flow plates 220 is to receive exhaust flowing inside the exhaust passage (along X-axis as indicated by arrows 228) and direct the exhaust into the gap 362 between the pair of flow plates 220. In addition, the plurality of perforations 222 direct the exhaust into the gap 362 in a direction orthogonal (along Z-axis, as indicated by arrows 370, and 371) to the direction of flow of exhaust inside the exhaust passage. It may be appreciated that the direction of flow of exhaust into the gap 362 via the first perforation 364 in the first flow plate 352 (as indicated by arrow 371) is opposite to the direction of flow of exhaust into the gap 362 via the second perforation 368 formed on the second flow plate 354 (as indicated by arrow 370).

The exhaust inside the gap 362 between the flow plates 220 then flows towards the flow entrance 356 in a direction opposite (as indicated by arrow 372) to the direction of flow of exhaust inside the exhaust passage (as indicated by arrow 228). It may be appreciated that the direction of flow of exhaust towards the flow entrance 356 is additionally orthogonal to the direction of flow of exhaust into the gap 362 via the plurality of perforations 222.

Exhaust flowing towards the flow entrance 356 is then directed into the housing 204 through the flow entrance 356 towards the sensor element 218 that is suspended within the housing 204. Specifically, exhaust flows into the housing 204 from the gap 362 through the flow entrance 356 in a direction opposite to exhaust flow inside the exhaust passage. Inside the housing 204, the sensor element 218 is suspended such that the electrodes 232 formed on the substrate 230 are positioned facing the flow entrance 356. Thus, the exhaust flowing into the housing 204 through the flow entrance 356 flows towards the electrodes 232 in a direction opposite to the direction of exhaust flow inside the exhaust passage (arrow 228). In this way, soot particles in the exhaust are accumulated across the electrodes 232 and an output of the PM sensor assembly 202 is generated. Based on the output of the PM sensor assembly 202, the filtering capabilities of a particulate filter positioned upstream of the PM sensor assembly 202 may be estimated, as explained later with reference to FIG. 8.

The main idea behind rotating the PM sensor assembly 202 inside the exhaust passage is to position the PM sensor assembly 202 such that the flow entrance 356 is placed on the downstream side where the static pressure is higher. As a result, more exhaust is drawn into the assembly through the perforations on the flow plate and hence an increased amount of exhaust flows thought the flow entrance into the assembly. Thus, a larger amount of particulates in the exhaust may be detected by the sensor element positioned facing the flow entrance. In this way, the sensitivity of the PM sensor assembly to detecting incoming soot particulates may be increased. Exhaust inside the housing 204 is then directed towards an exit 224 located at the bottom of the housing 204. In one example, the exit 224 may be a circular hole of diameter smaller or equal to the diameter D of the housing 204.

Thus, an example A particulate matter (PM) sensor, includes a protection tube or housing having a sensor element, a pair of plates having perforations, the pair of plates coupled to one side of the protection tube and separated from each other by a gap, a flow entrance formed on the one side of the protection tube, the flow entrance contiguous with the gap and positioned in between the pair of plates, the sensor element facing the flow entrance, a sensor cap and a gasket holder coupling the protection tube to an exhaust pipe, and a bearing arranged between an inner surface of the sensor cap and an outer surface of the gasket holder rotatably mounting the PM sensor to the exhaust pipe. Additionally or alternatively, the bearing may be configured to rotate the PM sensor along a central axis of the PM sensor that is orthogonal to a direction of exhaust flow inside the exhaust pipe. Additionally or alternatively, the pair of plates may be parallel to each other and further parallel to the direction of exhaust flow inside the exhaust pipe. Additionally or alternatively, the perforations on the pair of plates may be configured to receive exhaust from the exhaust pipe, direct the exhaust received into the gap in a direction orthogonal to the direction of exhaust flow inside the exhaust pipe, and then direct the exhaust in the gap towards the sensor element through the flow entrance formed on the protection tube, the flow entrance configured to direct the exhaust from the gap towards the sensor element in a direction opposite to the direction of exhaust flow inside the exhaust pipe. Additionally or alternatively, an exit at bottom of the protection tube may be configured to direct exhaust out of the PM sensor towards the exhaust pipe in a direction orthogonal to the direction of exhaust flow inside the exhaust pipe. Additionally or alternatively, the assembly may include a controller with computer readable instructions stored on non-transitory memory for applying a first voltage to a pair of electrodes formed on a first surface of the sensor element to accumulate exhaust PM across the pair of electrodes, estimating a load on the sensor element based on a current generated in the sensor element, and responsive to the load being higher than a threshold, applying a second voltage to a heating element formed on a second, opposite surface of the sensor element to regenerate the sensor.

As described previously, the flow plates 220 get deflected by the incoming exhaust and rotate the PM sensor assembly 202 passively inside the exhaust passage to align the flow entrance on the downstream side. However, it may be possible to rotate the PM sensor assembly actively using a motor as explained below.

Returning to FIG. 2, the PM sensor assembly 202 optionally includes a motor 238 that is controlled by a controller (such as controller 12 of FIG. 1). In one example, the motor 238 may be an electric motor. In another example, the motor for actuating the PM sensor assembly 202 may be an alternate type of motor/actuator in electronic communication with the controller 12.

Controller 12 may send signals for rotating the PM sensor assembly 202 to motor 238. These signals may include commands to rotate the PM sensor assembly 202 in a clockwise direction or an anti-clockwise direction about the central axis Y-Y'. The PM sensor assembly 202 may be rotated about the central axis Y-Y' inside the exhaust passage 206 via the bearing 212 based on estimated and/or sensed exhaust flow conditions. Exhaust flow conditions may include one or more of exhaust flow direction, exhaust flow rate, soot load on sensor assembly, exhaust temperature, and the like. Exhaust flow conditions may be estimated based on output of sensors mounted in the exhaust passage. As such, the controller may determine the exhaust flow conditions, and determine the amount of rotation needed, and subsequently adjust an output of the motor to rotate the PM sensor assembly by the desired amount. Rotating the PM sensor assembly includes actuating the motor 238 to rotate the assembly 202 about the central axis Y-Y' in order to position the flow entrance (flow entrance 356 shown in FIG. 3B) towards the downstream side facing away from the onslaught of incoming exhaust. The advantage of positioning the flow entrance on the downstream side is that the static pressure is higher in the downstream side, and more exhaust may be able to enter via the flow entrance and flow towards the sensor element 218 positioned inside the housing 204.

Thus, an example PM sensor assembly may optionally include a motor and a controller with computer readable instructions stored on non-transitory memory for actuating the motor to rotate the PM sensor such that the flow entrance is positioned on a downstream side of the PM sensor to direct the exhaust into the PM sensor through the flow entrance in a direction opposite to the direction of flow of exhaust inside the exhaust pipe.

In one example, the controller may determine the direction of exhaust flow inside the exhaust passage based on the outputs received from one or more sensors such as flow rate sensors, temperature sensors and pressure sensors positioned at different locations along the exhaust passage. When the direction of exhaust flow changes, the controller 12 may actuate the motor 238 to rotate the PM sensor assembly 202. While rotating the PM sensor assembly 202, the controller 12 may additionally monitor the output of the PM sensor assembly 202. In one example, the controller 12 may rotate the PM sensor assembly 202 by the same amount by which the exhaust flow direction changes by adjusting the output of the motor 238. As such, the PM sensor assembly 202 may be rotated in incremental steps to reach the desired rotation amount, or may be rotated in one swift rotation by the desired amount. In another example, the controller 12 may rotate the PM sensor assembly 202 until an instantaneous soot load on the PM sensor is higher. For example, when the PM sensor assembly 202 is rotated, the instantaneous soot load may be determined. The PM sensor assembly 202 may be rotated in a first direction in smaller increments. If the instantaneous soot load in the next position is higher than the soot load in the previous position, then the PM sensor assembly 202 may be rotated by the smaller increment in the same direction. However, in the next incremental rotation, if the instantaneous soot load is smaller than the previously measured soot load, then the PM sensor assembly 202 may be rotated in an opposite direction, and the PM sensor assembly 202 may be returned to the previous position by rotating by the same incremental amount but in the opposite direction. In this way, the PM sensor assembly 202 may be rotated such that the flow entrance is adaptively positioned to increase exhaust flow into the assembly and thereby increase the sensitivity of the assembly to detect soot particulate in the exhaust stream. In some example embodiments wherein the motor is coupled to the assembly, the flow plates may not be attached to the assembly. In such examples, the controller may actively rotate the assembly and automatically position the flow entrance on the downstream side thus allowing more exhaust to directly enter the assembly via the flow entrance.

As such, the exhaust may enter the flow entrance by reversing the direction of flow as shown in FIG. 4. Turning to FIG. 4, a schematic view 400 shows exhaust flow through a rotatable PM sensor assembly 402. Specifically, view 400 depicts exhaust flowing into the PM sensor assembly 402 via a flow entrance 422 formed along one side of the assembly.

The PM sensor assembly 402 may be an example of PM sensor 106 of FIG. 1 and/or PM sensor assembly 202 of FIGS. 2, 3A and 3B. As such, the details of the PM sensor assembly 402 may be similar to the PM sensor assembly 202 of schematic view 200 described with reference to FIGS. 2, 3A, and 3B. The flow entrance 422 may be an example of flow entrance 356 shown in FIG. 3B.

To summarize, the PM sensor assembly 402 includes a hollow cylindrical housing 404 rotatably mounted onto an exhaust passage 406 via bearing (not visible in the view 400) arranged between a sensor boss 408, the housing 404 and the exhaust passage 406. In one example, a plurality of ball bearings may be arranged concentrically to allow for reduced friction when the PM sensor assembly 402 is rotated inside the exhaust passage 406.

Additionally, the PM sensor assembly 402 includes a sensor element 410 inserted into the housing 404. The sensor element 410 is positioned inside the housing 404 such that electrodes 424 of the sensor element 410 is facing towards the flow entrance 422. In one example, the flow entrance 422 may include a rectangular slit or cut-out with a long axis being parallel to the central axis Y-Y', where a length of the slit may be larger than a width of the slit. Various shapes and sizes of the cut-out may be used without deviating from the scope of the disclosure. On either side of the flow entrance 422, flow plates 412 and 414 may be mounted the housing 404. Herein, the flow plates 412 and 414 are separated by a gap 416. In one example, the gap 416 is equal to the width of the flow entrance 422. In other examples, the gap 416 may be smaller than the width of the flow entrance 422.

For example, the exhaust may flow in a direction indicated by arrows 426 along the X-axis in a direction orthogonal to the central axis Y-Y'. Based on the direction of exhaust flow, the PM sensor assembly 402 may be rotated inside the exhaust passage. As previously described, the rotation may be a passive rotation based on the exhaust flow detected by the flow plates 412 and 414 or may be an active rotation brought about by the controller (such as controller 12 of FIGS. 1, 2, 3A and 3B). The main idea behind the rotation, be it active or passive, is that the flow entrance position 422 is rotated so that exhaust is configured to enter though the flow entrance 422 in a direction opposite to the direction of exhaust flow inside the exhaust passage.

As described previously, the flow plates 412 and 414 include a plurality of perforations configured to receive exhaust flowing inside exhaust passage. Herein, a plurality of perforations 418 may be formed along an edge of the flow plate 412 that is closer to the flow entrance 422. The plurality of perforations may include perforations of various shapes and sizes without deviating from the scope of the disclosure.

The plurality of perforations 418 formed on the flow plate 412 may receive exhaust flowing inside the exhaust passage 406 and may direct the received exhaust first into the gap 416 (as indicated by arrow 427) formed between the flow plates 412 and 414, and then towards the flow entrance 422 (as indicated by arrow 430). The direction of flow of exhaust into the gap 416 from the plurality of perforations 418 is orthogonal to the direction of flow of exhaust inside the exhaust passage 406 (as indicated by arrow 426). The direction of flow of exhaust from the gap 416 into the housing 404 though the flow entrance 422 (arrow 430) is opposite to the direction of flow of exhaust inside the exhaust passage 406 (arrow 426). Likewise, the plurality of perforations 420 formed on the flow plate 414 may receive exhaust flowing inside the exhaust passage 406 and may direct the received exhaust first into the gap 416 (as indicated by arrow 425) formed between the flow plates 412 and 414, and then towards the flow entrance 422 (as indicated by arrow 430). The direction of flow of exhaust into the gap 416 from the plurality of perforations 419 is orthogonal to the direction of flow of exhaust inside the exhaust passage 406 (as indicated by arrow 426). The direction of flow of exhaust into the gap 416 from the plurality of perforations 420 (arrow 425) is opposite to the direction of flow of exhaust into the gap via the perforations 418 formed on the flow plate 412 (arrow 427). Irrespective of how the exhaust enters the gap 416 (e.g., via the perforations 418 or via perforations 420), once inside the gap 416, the exhaust flows is directed towards the flow entrance 422 in a direction opposite (arrow 430) to the direction of flow of exhaust inside the exhaust passage (arrow 426).

Consider the situation when the direction of flow of exhaust inside the exhaust passage changes (e.g., due to changes in engine speed, load, cylinder deactivation, exhaust valve timing, exhaust recirculating though different passages, and the like) from a direction indicated by arrows 426 to a direction indicated by arrows 428. In one example, the flow plates 412 and 414 may be deflected in the clockwise direction when exhaust flow changes from a first direction (indicated by arrows 426) to a second direction (indicated by arrows 428). In another example, the change in the direction of exhaust flow from the first direction to the second direction may be detected based on the output of a plurality of sensors coupled to the exhaust passage as described previously. As such, when the direction of flow changes from the first direction (arrow 426) towards the second direction (arrow 428), the PM sensor assembly 402 may be rotated about the central axis Y-Y' via bearing as indicated by arrow 438. Rotating the PM sensor assembly 402 about the central axis Y-Y' includes rotating the assembly in a clockwise direction from the first direction towards the second direction in such a way that exhaust flow now enters the assembly via flow entrance 422 in a direction opposite to the second direction (arrow 428). An example method performed by the controller for rotating the PM sensor assembly based on an exhaust flow direction is described in FIG. 5. An example relationship between an output of the PM sensor assembly and an exhaust flow direction is shown in FIG. 9.

Figure 5:
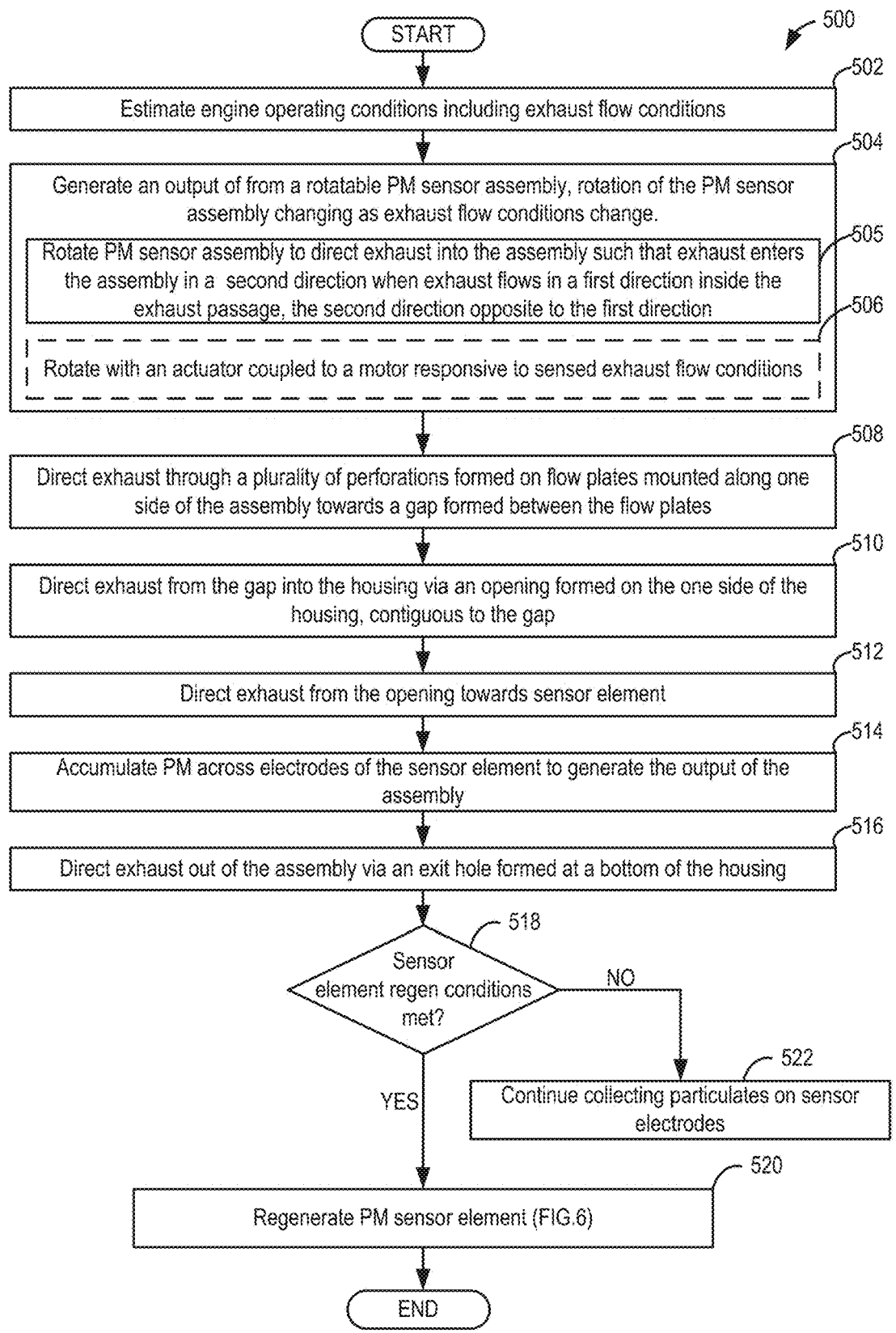
FIG. 5 shows a flow chart depicting an example method for accumulating particulates in the exhaust flow across the sensor element positioned within the housing of the PM sensor assembly.

Before proceeding to FIG. 5, it may be appreciated that FIGS. 1-4 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Turning now to FIG. 5, a method 500 for rotating a PM sensor assembly (such as a PM sensor 106 shown at FIG. 1, and/or PM sensor assembly 202 of FIG. 2, and/or PM sensor assembly 402 of FIG. 4, for example) is shown. Specifically, the PM sensor assembly may be rotatably mounted on an exhaust passage via a bearing. Herein, the PM sensor assembly may be rotated based on exhaust flow conditions.

Instructions for carrying out method 500 and the rest of the methods 600 and 700 included herein may be executed by a controller based on instructions stored on a memory of the controller and in conjunction with signals received from sensors of the engine system, such as the sensors described above with reference to FIG. 1. The controller may employ engine actuators of the engine system to adjust engine operation, according to the methods described below.

At 502, method 500 includes determining and/or estimating engine operating conditions including exhaust flow conditions. Engine operating conditions determined may include, for example, engine speed, exhaust flow direction, exhaust flow rate, engine temperature, exhaust air-fuel ratio, exhaust temperature, duration (or distance) elapsed since a last regeneration of the DPF, PM load on PM sensor, boost level, ambient conditions such as barometric pressure and ambient temperature, etc. Exhaust flow conditions include estimating or sensing one or more of soot load of PM sensor assembly, exhaust flow rate, exhaust flow direction, exhaust temperature, and the like. In one example, the controller may determine direction of exhaust flow based on outputs of one or more sensors such as exhaust flow rate sensor, exhaust temperature sensor, PM sensor, and the like. For example, based on changes in exhaust temperature as detected by multiple temperature sensors mounted along the exhaust passage, the controller may determine the exhaust flow direction. In another example, based on a change in exhaust flow rate as determined from exhaust flow rate sensors mounted in the exhaust passage, the exhaust flow direction may be estimated. In yet another example, based on a soot load of the PM sensor assembly, the direction of exhaust flow may be determined. Any changes in the output of the above sensors may be used to sense a change in exhaust flow direction, for example.

Method 500 proceeds to 504 where an output from a rotatable PM sensor assembly may be generated. Herein, the rotating of the assembly may change as the exhaust flow conditions changes. Rotating the PM sensor assembly includes rotating the assembly at 505 to direct exhaust into the assembly such that exhaust enters the assembly in a second direction when exhaust flows in a first direction inside the exhaust passage. Herein, the second direction is opposite to the first direction. For example, when the exhaust is flowing parallel to a central axis along the exhaust passage, the first direction may be represented as 0°. In such an example, the PM sensor assembly may be rotated about its central axis, such that the exhaust enters into the assembly after reversing its flow. Thus, exhaust enters the assembly at 180° with respect to the central axis of the exhaust passage. As such, rotating the PM sensor assembly includes rotating the assembly via bearing about the central axis of the assembly. Herein, the central axis of the assembly is orthogonal to the central axis of the exhaust passage. In one example, the rotation may be a passive rotation, where the exhaust flow automatically deflects flow plates attached to the assembly. Alternatively, at 506, method 500 includes actively rotating the assembly by actuating a motor coupled to the assembly. Herein, rotating via the motor includes adjusting an output of the motor to control the rotation of the PM sensor assembly. The output of the motor may be adjusted based on the output of the one or more above-mentioned sensors. When the exhaust is flowing in the first direction, the controller may rotate the PM sensor assembly by controlling the output of the motor to rotate the assembly to allow exhaust to enter the assembly in the second, opposite direction.

Rotating the PM sensor assembly (either actively or passively), includes rotating the assembly via the bearing mounting the assembly to the exhaust passage to direct exhaust into the assembly by performing 508 through 516 of method as described below.

At 508, method 500 includes rotating the assembly to direct exhaust through a plurality of perforations formed on flow plates along one side of the assembly towards a gap formed between the flow plates. Herein, the flow plates are parallel plates attached to one side of the assembly (specifically to a cylindrical housing of the assembly), and include a series of perforations configured to direct exhaust in a direction orthogonal to the first direction into the gap formed between the flow plates.

Next at 510, method 500 includes directing the exhaust from the gap into the PM sensor assembly via an opening formed on the one side of the housing of the assembly. Specifically, the exhaust is directed from the gap into the opening in the second opposite direction, wherein the second direction is opposite to the first direction. As such, the opening is formed between the flow plates on the one side of the housing and is contiguous with the gap formed between the flow plates. Said another way, the gap is fluidically coupled to the inside of the housing via the opening formed on the one side of the housing. In this way, the opening of the housing is positioned on a downstream side where the static pressure is higher. Thus, an increased amount of exhaust enters the assembly though the opening. In addition, larger particulates and water droplets in the exhaust remain unaffected by the higher static pressure and are blocked by the flow plates. Thus, the larger particulates and water droplets do not enter the PM sensor assembly via the opening, thereby reducing sensor errors due to these particulates depositing on the sensitive electrode surface, for example.

Next at 512, method 500 includes directing the exhaust through the opening towards a sensor element. Herein, the sensor element includes electrodes formed on a first surface, and a heating element formed on a second opposite surface. The sensor element is suspended inside such that the electrodes are facing the opening. In one example, a length of the sensing portion of the sensor electrodes is substantially equal to a length of the opening. Thus, soot particles in the exhaust are directed towards the sensor electrodes. Method 500 proceeds to 514.

At 514, method 500 includes accumulating PM across electrodes of the sensor element. Herein, the electrodes may include interdigitated positive and negative electrodes formed on a substrate of the sensor element. The controller applies a voltage to the electrodes of the sensor element to accumulate PM across the electrodes. As PM or soot particles get deposited between the interdigitated electrodes, the current measured between the electrodes may start to increase, which is measured by a measurement device. The controller may be able to determine the current and infer a corresponding PM or soot load on the interdigitated electrodes of the sensor element of the PM sensor assembly. By monitoring the load on the sensor element, the exhaust soot load downstream of the DPF may be determined, and thereby used to diagnose and monitor the health and functioning of the DPF (as described in FIG. 7).

Method 500 then proceeds to 516. At 516, method 500 includes directing exhaust out of the assembly via an exit hole formed at the bottom of the housing. Herein, the exit hole is configured to direct the exhaust out of the assembly such that exhaust exits via the home in a direction orthogonal to each of the first direction and the second direction. Method proceeds to 518.

At 518, method 500 includes determining if the sensor element regeneration conditions are met. Specifically, when the soot load on the PM sensor assembly is greater than the threshold, or when a resistance of the PM sensor assembly (adjusted for temperature) drops to a threshold resistance, or when a current of the PM sensor assembly is greater than a threshold current, PM sensor regeneration conditions may be considered met. In some examples, if a threshold time has elapsed since an immediately previous sensor regeneration, regeneration condition may be considered met. The PM sensor assembly may require regeneration to enable further PM detection.

Figure 6:
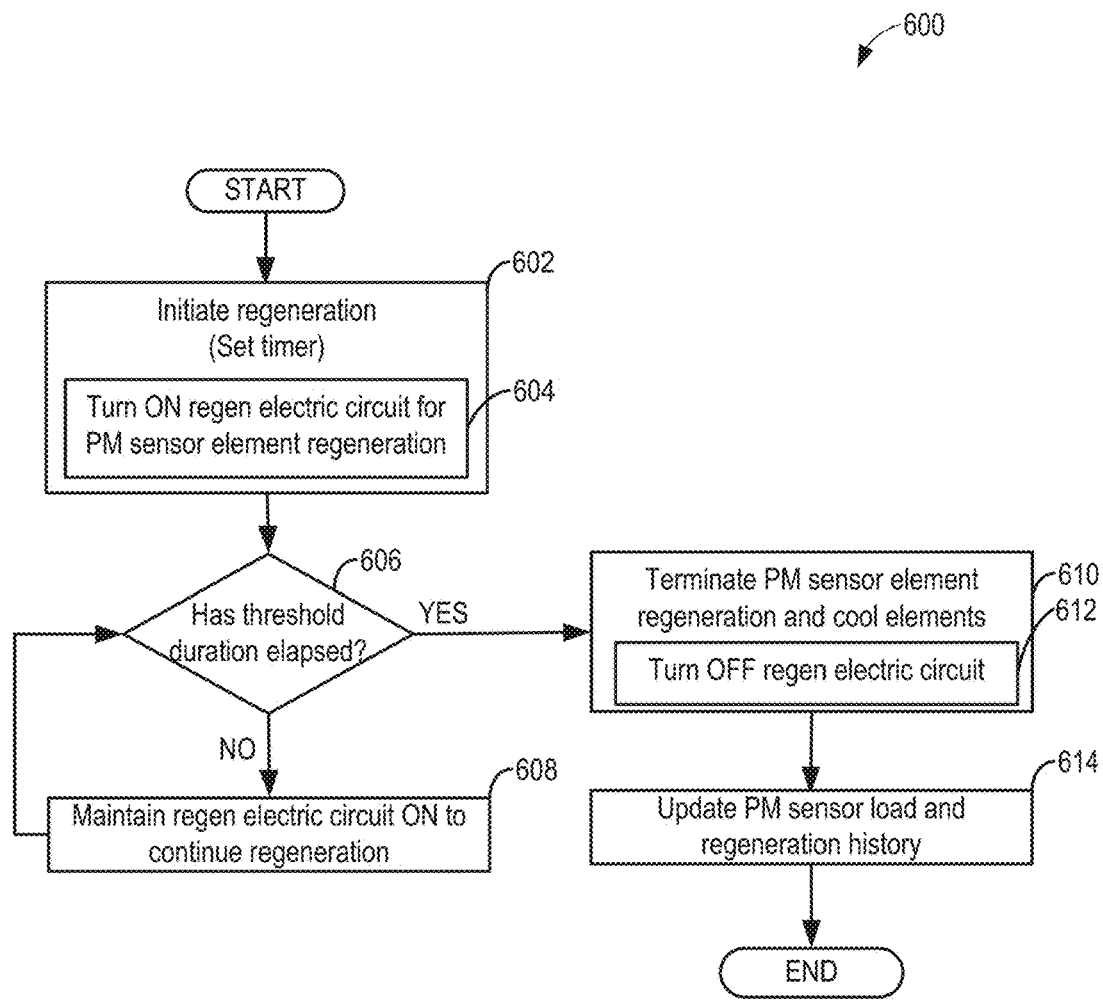
FIG. 6 is a flow chart depicting an example method for regenerating the sensor element of the PM sensor assembly.

If regeneration conditions are met (e.g., "YES" at 518), then method 500 proceeds to 520 where the PM sensor assembly may be regenerated by performing a method described in FIG. 6. Briefly, regeneration of the PM sensor assembly may be initiated by heating up the sensor. The PM sensor assembly may be heated by actuating a heating element coupled thermally to the substrate of the sensor electrodes, for example. Herein, the controller may close the switch in a regeneration circuit, thereby applying a voltage to the heating element, causing the heating elements to heat up. Further, the controller may not apply voltages to the sensor electrodes while regenerating the sensor. Thus, the sensor electrodes may not accumulate soot during the sensor regeneration. As such, the heating element may be actuated until the soot load of the sensor has been sufficiently reduced by oxidation of the carbon particles between the electrodes. However, if PM sensor regeneration conditions are not met (e.g., "NO" at 518), then method proceeds to 522 where the particulates may continue to be collected on the sensor electrodes and the method ends.

Thus, an example method includes while exhaust is flowing through an exhaust passage, generating an output from a rotatable particulate matter (PM) sensor assembly coupled to the exhaust passage, rotation of the rotatable PM sensor assembly changing as exhaust flow conditions change. Additionally or alternatively, the rotatable PM sensor assembly may include a cylindrical housing capable of rotating via a bearing along a central axis of the cylindrical housing assembly to increase particulate matter accumulation on a sensor element held inside in the cylindrical housing, the central axis being orthogonal to exhaust flow through the exhaust passage. Additionally or alternatively, the exhaust flow through the exhaust passage may be in a first direction, and wherein rotating the PM sensor assembly to increase PM accumulation may include rotating the PM sensor assembly to direct exhaust into the PM sensor assembly in a second direction, opposite the first direction, the exhaust directed into the PM sensor assembly through a plurality of perforations formed on flow plates mounted to the cylindrical housing of the PM sensor assembly. Additionally or alternatively, the flow plates may include a pair of plates mounted along one side of the cylindrical housing of the PM sensor assembly such that a gap is formed between the pair of plates. Additionally or alternatively, the exhaust may be first directed into the gap through the plurality of perforations, then from the gap into the cylindrical housing via an opening formed on the one side of the cylindrical housing, the opening contiguous to the gap. Additionally or alternatively, the exhaust may be directed from the opening towards the sensor element, the sensor element suspended from a top of the cylindrical housing, and wherein PM in the exhaust are accumulated across electrodes formed on a first surface of the sensor element to generate the output of the PM sensor assembly, the first surface closer to the opening of the cylindrical housing. Additionally or alternatively, the exhaust may be directed out of the PM sensor assembly via an exit hole formed at a bottom of the cylindrical housing. Additionally or alternatively, the rotating may include rotating with an actuator responsive to sensed exhaust flow conditions. Additionally or alternatively, the sensed exhaust flow conditions include one or more of a soot load, an exhaust flow rate, and an exhaust temperature of the exhaust flow.

Turning now to FIG. 9, map 900 shows an example relationship between an exhaust flow direction, a position of a rotatable PM sensor assembly, and an output of a PM sensor assembly. The first plot 902 of 900 shows the exhaust flow direction as determined by one or more of a flow rate sensor, a temperature sensor, and the like positioned at multiple locations inside an exhaust passage. The second plot 908 shows the position of the rotatable PM sensor assembly relative to the exhaust flow direction. The third plot 912 shows the output of the rotatable PM sensor assembly. The dashed line 910 indicates the output of a fixed PM sensor assembly wherein the PM sensor assembly position is fixed with respect to the exhaust flow direction. For each plot, time is depicted along the x (horizontal) axis while values of each respective parameter are depicted along the y (vertical) axis.

Between time t0 and t1, the exhaust flow inside the exhaust passage is in a first direction (plot 902). The rotatable PM sensor assembly may be positioned at position 1 (plot 908) so that exhaust enters the PM sensor assembly in a direction opposite to the first direction. Specifically, exhaust enters through a plurality of perforations on flow plates into a gap between the flow plates. Subsequently, the exhaust reverses its flow direction and flows towards a flow entrance positioned between the flow plates. Thereafter, the exhaust enters through the flow entrance towards a sensor element, and soot particles start to accumulate on the sensor element. The advantage of this is that more exhaust enters the assembly, and more particulates are accumulated across electrodes of the sensor element. As a result, the output of the PM sensor (plot 912) increases. In one example, the output of the PM sensor assembly may be the load on the sensor element. The controller may estimate the load of the assembly based on resistance/current change across the electrodes of the sensor element. The PM sensor assembly may be maintained in the first position as long as exhaust flows in the first direction.

However, at time t2, the exhaust flow direction changes from the first direction towards a second, different direction. Between time t2 and t3, the exhaust flow gradually changes from the first direction to the second direction. Accordingly, the PM sensor assembly may be rotated from the first direction towards the second direction. In one example, the flow plates may be deflected by the exhaust flow, and accordingly the PM sensor assembly may be gradually rotated towards the second direction. The amount of deflection of the flow plates by the exhaust flow may depend on the exhaust flow rate, for example. A higher flow rate may deflect the flow plates by a larger amount, and a lower flow rate may deflect the flow plates by a smaller amount. In another example, a controller may actuate a motor coupled to the PM sensor assembly to rotate the PM sensor assembly (by performing a method described in FIG. 5, for example) from the first direction towards the second direction. Herein, the amount of rotation may be controlled by controlling the output of the motor, for example. As the PM sensor assembly is rotated from the first direction towards the second direction, the output of the PM sensor assembly (plot 912) may continue to increase. However, if the PM sensor assembly is fixed to the exhaust passage, the change in flow direction may cause the output of the PM sensor assembly to decrease (plot 910). The reason being, the flow entrance may no longer be located on a higher static side, and the amount of exhaust gas entering the PM sensor assembly may be reduced. As a result, soot particulates captured across the electrodes will also drop, leading to a decreased PM sensor assembly output (plot 910). The advantage of the rotatable PM sensor assembly over the fixed assembly is that the rotatable assembly may be able to accurately detect soot particulates in the exhaust stream, independent of the exhaust flow direction.

Between t2 and t3, the exhaust flow is in the second direction (plot 902), and accordingly, the PM sensor assembly may be maintained at the second position (plot 908). Exhaust may continue to enter in a direction opposite to the second direction, and the output of the PM sensor assembly may continue to increase (plot 912). As explained earlier, the output of the PM sensor assembly may continue to decrease (plot 910).

Between t3 and t4, the exhaust flow direction may change from the second direction towards the first direction (plot 902). As a result, the rotatable PM sensor assembly position may be adjusted. Adjusting the rotatable PM sensor assembly includes rotating the assembly (either passively or actively, as described earlier) from the second direction to the first direction (plot 908). Herein, the rotation of the assembly allows for exhaust to enter the assembly in a direction opposite to the first direction. As a result, increased soot particulates are captures across the sensor electrodes and the output of the PM sensor assembly continues to increase (plot 912). As such, the direction of rotation of the assembly between t3 and t4 is opposite to the direction of rotation that occurred between t1 and t2. As a comparison, the output of the fixed PM sensor assembly would continue to decrease (plot 910).

Thus, an example PM sensor assembly may include a hollow, cylindrical tube rotatably mounted to an exhaust passage via ball bearings and rotatable about a central axis, a sensor element coaxial with the central axis and coupled to a tube top, a cut-out only one side of the tube, and a pair of parallel flow plates coupled to the one side of the tube and separated by a gap defined by a width of the cut-out. Additionally or alternatively, a first plate of the pair of parallel flow plates may be coupled to a first edge of the cut-out, and a second plate of the pair of parallel flow plates may be coupled to a second edge of the cut-out, and wherein each of the first plate and the second plate includes perforations configured to direct exhaust into the gap formed between the pair of parallel flow plates in a direction orthogonal to a direction of exhaust flow inside the exhaust passage, and then direct the exhaust from the gap towards the sensor element through the cut-out in a direction opposite to the direction of exhaust flow inside the exhaust passage. Additionally or alternatively, the assembly may further comprise a motor and a controller with computer readable instructions stored on non-transitory memory for responsive to the direction of exhaust flow changing from a first direction to a second direction, rotating the PM sensor assembly by actuating the motor to rotate the PM sensor assembly by a certain amount from the first direction towards the second direction such that the exhaust enters the PM sensor assembly opposite to the second direction, and applying voltage to electrodes formed on the sensor element to accumulate exhaust PM across the electrodes, the exhaust directed into the PM sensor assembly orthogonally to the electrodes of the sensor element. Additionally or alternatively, the assembly may further comprise an exit hole formed on a bottom surface of the protection tube, the exit hole configured to direct the exhaust out of the PM sensor assembly in a direction orthogonal to the direction of exhaust flow inside the exhaust passage.

Thus, by rotating the PM sensor assembly based on sensed exhaust flow conditions, the soot loading of the assembly may be maintained at a constant rate and the dependence of the output of the PM sensor assembly on exhaust flow direction may be further reduced. Thus, the PM sensor sensitivity is independent of the direction of incoming exhaust flow, thereby measuring PM exiting the DPF more accurately and reliably. Thus, any leaks or degradation of the DPF may be detected more efficiently and effectively.

Turning now to FIG. 6, a method 600 for regenerating the PM sensor (such as a PM sensor 106 shown at FIG. 1, and/or PM sensor assembly 202 of FIG. 2, for example) is shown. Specifically, when the soot load on the PM sensor is greater than the threshold, or when a resistance of the PM sensor adjusted for temperature drops to a threshold resistance, the PM sensor regeneration conditions may be considered met, and the PM sensor may require regeneration to enable further PM detection. At 602, regeneration of the PM sensor may be initiated and the PM sensor may be regenerated by heating up the sensor at 604. The PM sensor may be heated by actuating a heating element until the soot load of the sensor has been sufficiently reduced by oxidation of the carbon particles between the electrodes. The PM sensor regeneration is typically controlled by using timers and the timer may be set for a threshold duration at 602. Alternatively, the sensor regeneration may be controlled using a temperature measurement of the sensor tip, or by the control of power to the heater, or any or all of these. When a timer is used for PM sensor regeneration, then method 600 includes checking if the threshold duration has elapsed at 606. If the threshold duration has not elapsed (e.g., "NO" at 606), then method 600 proceeds to 608 where the regeneration circuit may be kept ON to continue regeneration. If threshold duration has elapsed (e.g., "YES" at 606), then method 600 proceeds to 610 where the PM sensor regeneration may be terminated and the electric circuit may be turned off at 612. Further, the sensor electrodes may be cooled to the exhaust temperature for example. Method 600 proceeds to 614 where the PM sensor load and regeneration history may be updated and stored in memory. For example, a frequency of PM sensor regeneration and/or an average duration between sensor regenerations may be updated and the method ends.

The engine exhaust passage may include one or more PM sensors positioned upstream and/or downstream of the DPF for determining a soot load of the DPF. When the PM sensor is positioned upstream of the DPF, based on the resistance change following soot deposited on the plurality of electrodes of the PM sensor, a soot load on the sensor may be inferred. The soot load thus determined, may be used to update the soot load on the DPF, for example. If the soot load on the DPF is greater than a threshold for DPF regeneration, then the controller may adjust engine operating parameters to regenerate the DPF. Specifically, responsive to filter regeneration conditions being met, a temperature of the filter (or in the vicinity of the filter) may be sufficiently raised to burn off stored soot. This may include operating a heater coupled to the DPF, or raising a temperature of engine exhaust (e.g., by operating rich) flowed into the DPF.

Figure 7:
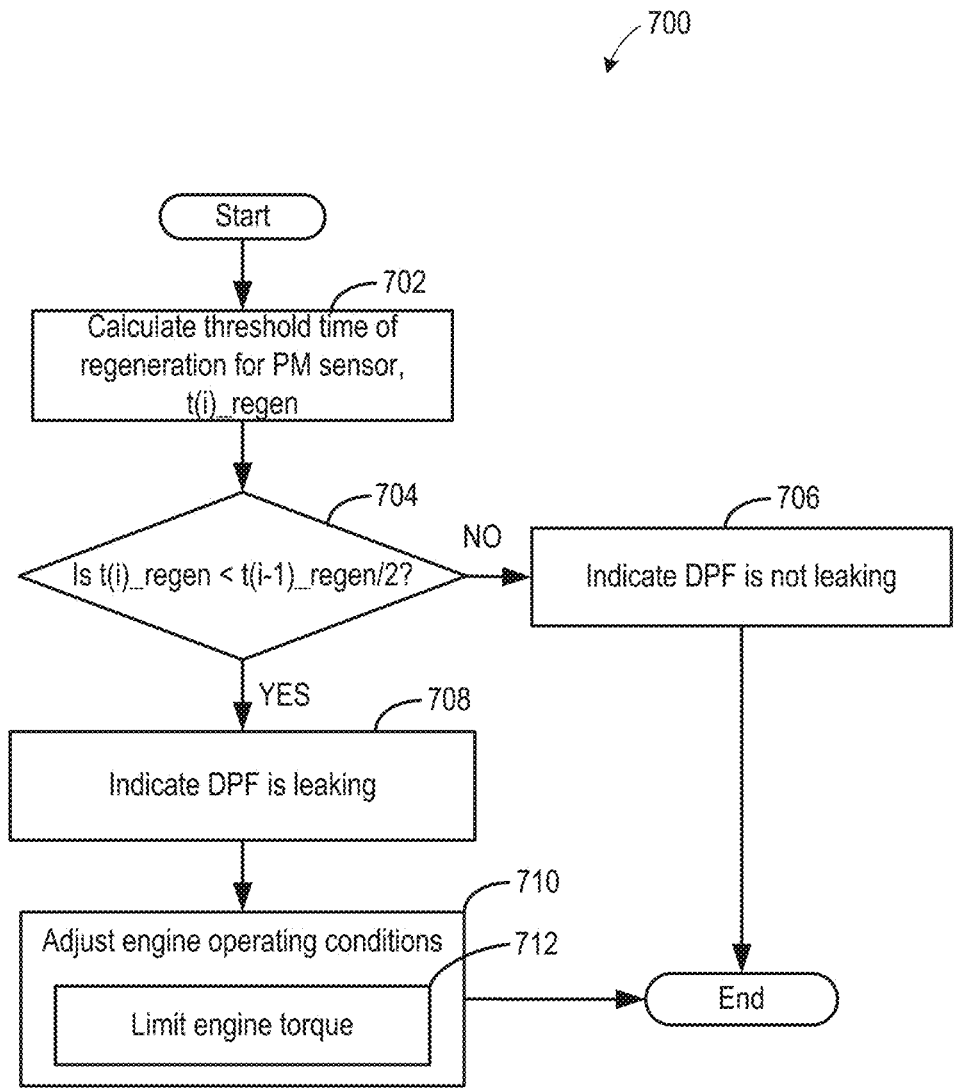
FIG. 7 shows a flow chart depicting an example method for diagnosing leaks in a particulate filter positioned upstream of the PM sensor assembly.

Turning now to FIG. 7, an example method 700 for diagnosing DPF function based on the regeneration time of the PM sensor is shown. At 702, it may be calculated by the controller, through calibration, the time of regeneration for the PM sensor, t(i)_regen, which is the time measured from end of previous regeneration to the start of current regeneration of the PM sensor. At 704, compare t(i)_regen to t(i−1)_regen, which is the previously calibrated time of regeneration of the PM sensor. From this, it may be inferred that the soot sensor may cycle through regeneration multiple times in order to diagnose the DPF. If the t(i)_regen is less than half the value of t(i−1) region, then at 708 indicate DPF is leaking, and DPF degradation signal is initiated. Alternatively, or additionally to the process mentioned above, the DPF may be diagnosed using other parameters, such as exhaust temperature, engine speed/load, etc. The degradation signal may be initiated by, for example, a malfunction indication light on diagnostic code. In addition, method 700 includes adjusting engine operation based on indicating leak in the DPF at 710. Adjusting engine operation may include limiting engine torque at 712, for example. In one example, responsive to detecting leak in the DPF, engine power and torque may be reduced. Reducing the engine power and torque may reduce the amount of PM emissions in the exhaust. For example, adjusting engine operation may include reducing fuel injected in a diesel engine under heavy load conditions thereby reducing torque. Additionally or alternatively, responsive to detecting leak in the DPF, an EGR usage may be decreased. Additionally or alternatively, an engine warning sign will appear on the dashboard to indicate the maximal distance vehicle can drive before DPF service check.

A current regeneration time of less than half of the previous regeneration time may indicate that the time for electric circuit to reach the R_regen threshold is significantly shorter, and thus the frequency of regeneration is higher. Higher frequency of regeneration in the PM sensor may indicate that the outflowing exhaust gas is composed of a higher amount of particulate matter than realized with a normally functionally DPF. Thus, if the change of regeneration time in the soot sensor reaches threshold, t_regen, in which the current regeneration time of the PM sensor is less than half of that of the previous regeneration time, a DPF degradation, or leaking, is indicated, for example via a display to an operator, and/or via setting a flag stored in non-transitory memory coupled to the processor, which may be sent to a diagnostic tool coupled to the processor. If the change in regeneration time of the soot sensor does not reach threshold t_regen, then at 706 DPF leaking is not indicated. In this way, leaks in a particulate filter positioned upstream of the particulate matter sensor may be detected based on a rate of deposition of the particulates on the particulate matter sensor electrodes.

Turning now to FIG. 8, map 800 shows an example relationship between soot load on the PM sensor and the soot load on the particulate filter. Specifically, map 800 shows a graphical depiction of the relationship between PM sensor regeneration and the soot load of the DPF, specifically how PM sensor regeneration may indicate DPF degradation. Vertical markers t0, t1, t2, t3, t4, t5 and t6 identify significant times in the operation and system of PM sensor and DPF.

The first plot of FIG. 8 shows a soot load on the PM sensor. As previously described, PM gets deposited across the positive and negative electrodes formed on a plate that is positioned inside a stepped assembly. As soot gets accumulated, a current measured across the electrodes beings to increase (or a resistance of the electrodes begins to decrease). The controller may be able to determine a soot load (plot 802) based on the current/resistance measured. As such, the soot load is at its lowest value at the bottom of the plots and increases in magnitude toward the top of the plot in the vertical direction. The horizontal direction represents time and time increases from the left to the right side of the plot. Horizontal marker 806 represents the threshold load for regeneration of the PM sensor in the top plot. Plot 804 represents the soot load on the DPF, and the horizontal marker 808 represents the threshold soot load of DPF in the second plot.

Between t0 and t1, a PM sensor regeneration cycle is shown. At time t0, the PM sensor is in a relatively clean condition, as measured by low PM load (plot 802). A controller coupled to the PM sensor determines the soot load of the PM sensor based on the current/resistance measured across the sensor electrodes, for example. When the controller determines the soot load to be small, it may send instructions to a regeneration circuit to end supplying heat, so that a detection circuit may begin detecting PM load accumulation. As PM load increases on the sensor, soot gets accumulated in the gap between the sensor electrodes.

Between t0 and t1, as PM continues to accumulate, the soot load (plot 802) increases accordingly and further soot load on DPF also increases (plot 804). In some examples, soot load on the DPF may be based on PM sensor load when PM sensor is located upstream of DPF, for example.

At t1, the soot load on the PM sensor (plot 802) reaches the threshold load for regeneration of the PM sensor (marker 806). The threshold load may a load at which the sensor may require regeneration. At t1, PM sensor regeneration may be initiated as explained earlier. Briefly, the controller may close a switch in the electric circuit to apply voltage to the heating elements formed along the inner surface of the central element, for example. In addition, the PM sensor may not be operated in PM accumulation mode, thus the controller may not apply any voltage to the sensor electrodes.

Thus, between t1 and t2, the PM sensor may be regenerated by turning on the electric circuit for regeneration. At t2, the PM sensor may be sufficiently cool, and may begin to accumulate soot and continue accumulating between t2 and t3 (DPF regeneration cycle), for example. During time between t2 and t3, DPF soot load continues to increase (plot 804). However, at t3, the soot load on the DPF (plot 804) reaches the threshold soot load for DPF regeneration (marker 808). Between t3 and t4, the DPF may be regenerated to burn off the soot deposited on the DPF. Further at t4, the PM sensor regeneration frequency may be compared with a previously estimated regeneration frequency of the PM sensor. Based on the PM sensor regeneration frequency remaining similar to previous cycles, the DPF may be determined to be not leaking. In this way, based on PM sensor output, DPF health may be monitored and diagnosed for leaks.

Between t5 and t6, another DPF cycle is shown. Herein, between t5 and t6, the soot load on the DPF gradually increases (plot 804). During this time, the soot load on the PM sensor (plot 802) may be monitored. Plot 802 shows the PM sensor going through multiple regeneration cycles as described earlier. However, the frequency of regeneration of the PM sensor has nearly doubled (plot 802). The higher frequency of regeneration in the PM sensor may indicate that the outflowing exhaust gas is composed of a higher amount of particulate matter than realized with a normally functional DPF. Therefore at t6, DPF leakage may be indicated.

In this way, a more accurate measure of the exhaust PM load, and thereby the DPF soot load can be determined. As such, this increases the efficiency of filter regeneration operations. In addition, by enabling more accurate diagnosis of an exhaust DPF, exhaust emissions compliance may be increased. As such, this reduces the high warranty costs of replacing functional particulate filters and exhaust component life is extended.

In this way, by rotating the PM sensor assembly based on sensed exhaust flow conditions, the soot loading of the assembly may be maintained at a constant rate and the dependence of the output of the PM sensor assembly on exhaust flow direction may be further reduced. The technical effect of rotating the PM sensor assembly via the bearing inside the exhaust passage is that the rate of deposition of particulates on the PM sensor electrodes remain near constant. Thus, the PM sensor sensitivity is independent of the direction of incoming exhaust flow, thereby measuring PM exiting the DPF more accurately and reliably. Thus, any leaks or degradation of the DPF may be detected more efficiently and effectively. Another technical effect of including flow plates is that larger particulates and/or water droplets may be trapped by the flow plates. Therefore, the sensor element may be protected from impingement of water droplets and larger particulates. Overall, these characteristics of the sensor may cause an output of the sensor to be more accurate, thereby increasing the accuracy of estimating particulate loading on a particulate filter.

The systems and methods described above also provide for a method, the method comprising while exhaust is flowing through an exhaust passage, generating an output from a rotatable particulate matter (PM) sensor assembly coupled to the exhaust passage, rotation of the rotatable PM sensor assembly changing as exhaust flow conditions change. In a first example of the method, the method may additionally or alternatively include wherein the rotatable PM sensor assembly includes a cylindrical housing capable of rotating via a bearing along a central axis of the cylindrical housing assembly to increase particulate matter accumulation on a sensor element held inside the cylindrical housing, the central axis being orthogonal to exhaust flow through the exhaust passage. A second example of the method optionally includes the first example, and further includes wherein the exhaust flow through the exhaust passage is in a first direction, and wherein rotating the PM sensor assembly to increase PM accumulation includes rotating the PM sensor assembly to direct exhaust into the PM sensor assembly in a second direction, opposite the first direction, the exhaust directed into the PM sensor assembly through a plurality of perforations formed on flow plates mounted to the cylindrical housing of the PM sensor assembly. A third example of the method optionally includes one or more of the first and the second examples, and further includes wherein the flow plates include a pair of plates mounted along one side of the cylindrical housing of the PM sensor assembly such that a gap is formed between the pair of plates. A fourth example of the method optionally includes one or more of the first through the third examples, and further includes wherein the exhaust is first directed into the gap through the plurality of perforations, then from the gap into the cylindrical housing via an opening formed on the one side of the cylindrical housing, the opening contiguous to the gap. A fifth example of the method optionally includes one or more of the first through the fourth examples, and further includes wherein the exhaust is directed from the opening towards the sensor element, the sensor element suspended from a top of the cylindrical housing, and wherein PM in the exhaust are accumulated across electrodes formed on a first surface of the sensor element to generate the output of the PM sensor assembly, the first surface closer to the opening of the cylindrical housing. A sixth example of the method optionally includes one or more of the first through the fifth examples, and further includes wherein the exhaust is directed out of the PM sensor assembly via an exit hole formed at a bottom of the cylindrical housing. A seventh example of the method optionally includes one or more of the first through the sixth examples, and further includes wherein the rotating includes rotating with an actuator responsive to sensed exhaust flow conditions. An eighth example of the method optionally includes one or more of the first through the seventh examples, and further includes wherein the sensed exhaust flow conditions includes one or more of a soot load, an exhaust flow rate, and an exhaust temperature of the exhaust flow.

The systems and methods described above provide for a particulate matter sensor comprising a protection tube having a sensor element, a pair of plates having perforations, the pair of plates coupled to one side of the protection tube and separated from each other by a gap, a flow entrance formed on the one side of the protection tube, the flow entrance contiguous with the gap and positioned in between the pair of plates, the sensor element facing the flow entrance, a sensor cap and a gasket holder coupling the protection tube to an exhaust pipe, and a bearing arranged between an inner surface of the sensor cap and an outer surface of the gasket holder rotatably mounting the PM sensor to the exhaust pipe. In a first example of the particulate matter sensor assembly, the sensor may additionally or alternatively include wherein the bearing is configured to rotate the PM sensor along a central axis of the PM sensor that is orthogonal to a direction of exhaust flow inside the exhaust pipe. A second example of the particulate matter sensor optionally includes the first example and further includes wherein the pair of plates are parallel to each other and further parallel to the direction of exhaust flow inside the exhaust pipe. A third example of the particulate matter sensor optionally includes one or more of the first and the second examples, and further includes wherein the perforations on the pair of plates are configured to receive exhaust from the exhaust pipe, direct the exhaust received into the gap in a direction orthogonal to the direction of exhaust flow inside the exhaust pipe, and then direct the exhaust in the gap towards the sensor element through the flow entrance formed on the protection tube, the flow entrance configured to direct the exhaust from the gap towards the sensor element in a direction opposite to the direction of exhaust flow inside the exhaust pipe. A fourth example of the particulate matter sensor optionally includes one or more of the first through the third examples, and further includes a motor and a controller with computer readable instructions stored on non-transitory memory for actuating the motor to rotate the PM sensor such that the flow entrance is positioned on a downstream side of the PM sensor to direct the exhaust into the PM sensor through the flow entrance in a direction opposite to the direction of flow of exhaust inside the exhaust pipe. A fifth example of the particulate matter sensor optionally includes one or more of the first through the fourth examples, and further includes wherein the controller includes further instructions for applying a first voltage to a pair of electrodes formed on a first surface of the sensor element to accumulate exhaust PM across the pair of electrodes, estimating a load on the sensor element based on a current generated in the sensor element, and responsive to the load being higher than a threshold, applying a second voltage to a heating element formed on a second, opposite surface of the sensor element to regenerate the sensor. A sixth example of the particulate matter sensor optionally includes one or more of the first through the fifth examples, and further includes wherein an exit at bottom of the protection tube is configured to direct exhaust out of the PM sensor towards the exhaust pipe in a direction orthogonal to the direction of exhaust flow inside the exhaust pipe.

The systems and methods described above provide for a particulate matter sensor comprising a hollow, cylindrical tube rotatably mounted to an exhaust passage via ball bearings and rotatable about a central axis, a sensor element coaxial with the central axis and coupled to a tube top, a cut-out only one side of the tube, and a pair of parallel flow plates coupled to the one side of the tube and separated by a gap defined by a width of the cut-out. In a first example of the particulate matter sensor assembly, the sensor may additionally or alternatively include wherein a first plate of the pair of parallel flow plates is coupled to a first edge of the cut-out, and a second plate of the pair of parallel flow plates is coupled to a second edge of the cut-out, and wherein each of the first plate and the second plate includes perforations configured to direct exhaust into the gap formed between the pair of parallel flow plates in a direction orthogonal to a direction of exhaust flow inside the exhaust passage, and then direct the exhaust from the gap towards the sensor element through the cut-out in a direction opposite to the direction of exhaust flow inside the exhaust passage. A second example of the particulate matter sensor assembly optionally includes the first example and further includes a motor and a controller with computer readable instructions stored on non-transitory memory for: responsive to the direction of exhaust flow changing from a first direction to a second direction, rotating the PM sensor assembly by actuating the motor to rotate the PM sensor assembly by a certain amount from the first direction towards the second direction such that the exhaust enters the PM sensor assembly opposite to the second direction, and applying voltage to electrodes formed on the sensor element to accumulate exhaust PM across the electrodes, the exhaust directed into the PM sensor assembly orthogonally to the electrodes of the sensor element. A third example of the particulate matter sensor assembly optionally includes one or more of the first and the second examples, and further comprising an exit hole formed on a bottom surface of the protection tube, the exit hole configured to direct the exhaust out of the PM sensor assembly in a direction orthogonal to the direction of exhaust flow inside the exhaust passage.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A particulate matter (PM) sensor, comprising:
a protection tube having a sensor element;
a pair of plates having perforations, the pair of plates coupled to one side of the protection tube and separated from each other by a gap;
a flow entrance formed on the one side of the protection tube, the flow entrance contiguous with the gap and positioned in between the pair of plates, the sensor element facing the flow entrance;
a sensor cap and a gasket holder for coupling the protection tube to an exhaust pipe; and
a bearing arranged between an inner surface of the sensor cap and an outer surface of the gasket holder for rotatably mounting the protection tube of the PM sensor to the exhaust pipe.

2. The PM sensor of claim 1, wherein the bearing is configured to rotate the protection tube of the PM sensor about a central axis of the PM sensor that is orthogonal to a direction of exhaust flow inside the exhaust pipe.

3. The PM sensor of claim 2, wherein the pair of plates are parallel to each other and further configured to be parallel to the direction of exhaust flow inside the exhaust pipe.

4. The PM sensor of claim 2, wherein the perforations on the pair of plates are configured to receive exhaust from the exhaust pipe, direct the exhaust received into the gap in a direction orthogonal to the direction of exhaust flow inside the exhaust pipe, and then direct the exhaust in the gap towards the sensor element through the flow entrance formed on the protection tube, the flow entrance configured to direct the exhaust from the gap towards the sensor element in a direction opposite to the direction of exhaust flow inside the exhaust pipe.

5. The PM sensor of claim 2, further comprising a motor and a controller with computer readable instructions stored on non-transitory memory for:
actuating the motor to rotate the protection tube of the PM sensor such that the flow entrance is positioned on a downstream side of the PM sensor to direct the exhaust into the PM sensor through the flow entrance in a direction opposite to the direction of flow of exhaust inside the exhaust pipe.

6. The PM sensor of claim 5, wherein the controller includes further instructions for:
applying a first voltage to a pair of electrodes formed on a first surface of the sensor element to accumulate exhaust PM across the pair of electrodes;
estimating a load on the sensor element based on a current generated in the sensor element; and
responsive to the load being higher than a threshold, applying a second voltage to a heating element formed on a second, opposite surface of the sensor element to regenerate the PM sensor.

7. The PM sensor of claim 2, wherein an exit at bottom of the protection tube is configured to direct exhaust out of the PM sensor towards the exhaust pipe in a direction orthogonal to the direction of exhaust flow inside the exhaust pipe.

8. A particulate matter (PM) sensor assembly, comprising:
a hollow, cylindrical tube rotatably mounted to an exhaust passage via ball bearings and rotatable about a central axis;
a sensor element coaxial with the central axis and coupled to a top of the tube;
a cut-out on one side of the tube; and
a pair of parallel flow plates coupled to the one side of the tube and separated by a gap defined by a width of the cut-out.

9. The assembly of claim 8, wherein a first plate of the pair of parallel flow plates is coupled to a first edge of the cut-out, and a second plate of the pair of parallel flow plates is coupled to a second edge of the cut-out, and wherein each of the first plate and the second plate includes perforations configured to direct exhaust into the gap formed between the pair of parallel flow plates in a direction orthogonal to a direction of exhaust flow inside the exhaust passage, and then direct the exhaust from the gap towards the sensor element through the cut-out in a direction opposite to the direction of exhaust flow inside the exhaust passage.

10. The assembly of claim 9, further comprising a motor and a controller with computer readable instructions stored on non-transitory memory for:
responsive to the direction of exhaust flow changing from a first direction to a second direction,
rotating the tube of the PM sensor assembly by actuating the motor to rotate the tube of the PM sensor assembly by a certain amount from the first direction towards the second direction such that the exhaust enters the PM sensor assembly in a direction opposite to the second direction; and
applying a voltage to electrodes formed on the sensor element to accumulate exhaust PM across the electrodes, the exhaust directed into the PM sensor assembly orthogonally to the electrodes of the sensor element.

11. The assembly of claim 9, further comprising an exit hole formed on a bottom surface of the tube, the exit hole configured to direct the exhaust out of the PM sensor assembly in a direction orthogonal to the direction of exhaust flow inside the exhaust passage.

* * * * *